(12) United States Patent
Hoang et al.

(10) Patent No.: US 12,357,452 B2
(45) Date of Patent: Jul. 15, 2025

(54) SEALING MEMBER FOR PROSTHETIC HEART VALVE

(71) Applicant: EDWARDS LIFESCIENCES CORPORATION, Irvine, CA (US)

(72) Inventors: Lien Huong Thi Hoang, San Juan Capistrano, CA (US); Son V. Nguyen, Irvine, CA (US); Hien Tran Ngo, Irvine, CA (US); Vivian Tran, Santa Ana, CA (US); Russell T. Joseph, Las Flores, CA (US); Dinesh L Sirimanne, Irvine, CA (US); Kevin D. Rupp, Irvine, CA (US); Diana Nguyen-Thien-Nhon, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/542,482

(22) Filed: Dec. 15, 2023

(65) Prior Publication Data
US 2024/0115375 A1    Apr. 11, 2024

Related U.S. Application Data

(63) Continuation of application No. 17/708,428, filed on Mar. 30, 2022, now Pat. No. 11,883,281, which is a
(Continued)

(51) Int. Cl.
*A61F 2/24* (2006.01)

(52) U.S. Cl.
CPC .......... *A61F 2/2409* (2013.01); *A61F 2/2418* (2013.01); *A61F 2230/0006* (2013.01);
(Continued)

(58) Field of Classification Search
CPC .................. A61F 2/2409; A61F 2/2418; A61F 2230/0006; A61F 2230/0069;
(Continued)

(56) References Cited

U.S. PATENT DOCUMENTS

| 30,912 A | 12/1860 | Hancock |
|---|---|---|
| 3,409,013 A | 11/1968 | Berry |

(Continued)

FOREIGN PATENT DOCUMENTS

| DE | 0144167 C | 9/1903 |
|---|---|---|
| DE | 2246526 A1 | 3/1973 |

(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.
(Continued)

*Primary Examiner* — Ann Hu
(74) *Attorney, Agent, or Firm* — Klarquist Sparkman, LLP; Joel B. German

(57) ABSTRACT

A prosthetic heart valve includes an annular frame that is radially collapsible and expandable between a radially collapsed configuration and a radially expanded configuration. The frame has a plurality of circumferentially extending rows of angled struts, each row of angled struts comprising angled struts arranged in a zig-zag pattern. The prosthetic heart valve further includes a leaflet structure positioned within the frame and secured thereto, and an outer sealing member mounted outside of the frame. The sealing member has an undulating outflow edge portion forming a plurality of triangular projections that are connected to and shaped to correspond to the zig-zag pattern of one of the rows of
(Continued)

angled struts. The outer sealing member is sized to fit snugly against the outer surface of the frame when the frame is in the expanded configuration.

16 Claims, 17 Drawing Sheets

Related U.S. Application Data continuation of application No. 16/120,112, filed on Aug. 31, 2018, which is a continuation-in-part of application No. 15/991,325, filed on May 29, 2018, now abandoned.

(60) Provisional application No. 62/513,348, filed on May 31, 2017.

(52) U.S. Cl.
CPC ............... *A61F 2230/0069* (2013.01); *A61F 2230/0076* (2013.01)

(58) Field of Classification Search
CPC ...... A61F 2230/0076; A61F 2220/0075; A61F 2250/0069; A61F 2002/0081; A61F 2002/0086; A61F 2/0077
See application file for complete search history.

(56) References Cited

U.S. PATENT DOCUMENTS

| | | | |
|---|---|---|---|
| 3,548,417 A | 12/1970 | Kisher | |
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 3,878,565 A | 4/1975 | Sauvage | |
| 4,035,849 A * | 7/1977 | Angell .................. | A61F 2/2409 264/222 |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,441,216 A | 4/1984 | Ionescu et al. | |
| 4,470,157 A | 9/1984 | Love | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,820,299 A | 4/1989 | Philippe et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,892,539 A | 1/1990 | Koch | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,346 A * | 3/1995 | Walker .................. | A61F 2/2409 623/2.41 |
| 5,397,351 A | 3/1995 | Pavcnik et al. | |
| 5,411,055 A | 5/1995 | Kane | |
| 5,411,552 A | 5/1995 | Andersen et al. | |
| 5,443,446 A | 8/1995 | Shturman | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely et al. | |
| 5,554,185 A | 9/1996 | Block et al. | |
| 5,558,644 A | 9/1996 | Boyd et al. | |
| 5,571,175 A | 11/1996 | Vanney et al. | |
| 5,584,803 A | 12/1996 | Stevens et al. | |
| 5,591,185 A | 1/1997 | Kilmer et al. | |
| 5,591,195 A | 1/1997 | Taheri et al. | |
| 5,607,464 A | 3/1997 | Trescony et al. | |
| 5,609,626 A | 3/1997 | Quijano et al. | |
| 5,628,792 A | 5/1997 | Lentell | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein et al. | |
| 5,769,812 A | 6/1998 | Stevens et al. | |
| 5,800,508 A | 9/1998 | Goicoechea et al. | |
| 5,840,081 A | 11/1998 | Andersen et al. | |
| 5,855,597 A | 1/1999 | Jayaraman | |
| 5,855,601 A | 1/1999 | Bessler et al. | |
| 5,855,602 A | 1/1999 | Angell | |
| 5,925,063 A | 7/1999 | Khosravi | |
| 5,957,949 A | 9/1999 | Leonhardt et al. | |
| 6,027,525 A | 2/2000 | Suh et al. | |
| 6,110,198 A | 8/2000 | Fogarty et al. | |
| 6,132,473 A | 10/2000 | Williams et al. | |
| 6,168,614 B1 | 1/2001 | Andersen et al. | |
| 6,171,335 B1 | 1/2001 | Wheatley et al. | |
| 6,174,327 B1 | 1/2001 | Mertens et al. | |
| 6,210,408 B1 | 4/2001 | Chandrasekaran et al. | |
| 6,217,585 B1 | 4/2001 | Houser et al. | |
| 6,221,091 B1 | 4/2001 | Khosravi | |
| 6,221,102 B1 | 4/2001 | Baker et al. | |
| 6,231,602 B1 | 5/2001 | Carpentier et al. | |
| 6,245,102 B1 | 6/2001 | Jayaraman | |
| 6,299,637 B1 | 10/2001 | Shaolian et al. | |
| 6,302,906 B1 | 10/2001 | Goicoechea et al. | |
| 6,338,740 B1 | 1/2002 | Carpentier | |
| 6,350,277 B1 | 2/2002 | Kocur | |
| 6,352,547 B1 | 3/2002 | Brown et al. | |
| 6,425,916 B1 | 7/2002 | Garrison et al. | |
| 6,440,764 B1 | 8/2002 | Focht et al. | |
| 6,454,799 B1 | 9/2002 | Schreck | |

(56) References Cited

U.S. PATENT DOCUMENTS

| | | | |
|---|---|---|---|
| 6,458,153 B1 | 10/2002 | Bailey et al. | |
| 6,461,382 B1 | 10/2002 | Cao | |
| 6,468,660 B2 | 10/2002 | Ogle et al. | |
| 6,482,228 B1 | 11/2002 | Norred | |
| 6,488,704 B1 | 12/2002 | Connelly et al. | |
| 6,527,979 B2 | 3/2003 | Constantz et al. | |
| 6,547,820 B1* | 4/2003 | Staudenmeier | D04B 21/02 264/103 |
| 6,569,196 B1 | 5/2003 | Vesely | |
| 6,582,462 B1 | 6/2003 | Andersen et al. | |
| 6,605,112 B1 | 8/2003 | Moll et al. | |
| 6,652,578 B2 | 11/2003 | Bailey et al. | |
| 6,689,123 B2 | 2/2004 | Pinchasik | |
| 6,716,244 B2 | 4/2004 | Klaco | |
| 6,729,356 B1 | 5/2004 | Baker et al. | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,769,161 B2 | 8/2004 | Brown et al. | |
| 6,783,542 B2 | 8/2004 | Eidenschink | |
| 6,830,584 B1 | 12/2004 | Seguin | |
| 6,878,162 B2 | 4/2005 | Bales et al. | |
| 6,893,460 B2 | 5/2005 | Spenser et al. | |
| 6,908,481 B2 | 6/2005 | Cribier | |
| 6,918,926 B2 | 7/2005 | Letort | |
| 6,936,067 B2 | 8/2005 | Buchanan | |
| 7,018,406 B2 | 3/2006 | Seguin et al. | |
| 7,018,408 B2 | 3/2006 | Bailey et al. | |
| 7,044,962 B2* | 5/2006 | Elliott | A61F 2/07 623/1.13 |
| 7,096,554 B2 | 8/2006 | Austin et al. | |
| 7,175,652 B2* | 2/2007 | Cook | A61F 2/07 623/1.13 |
| 7,225,518 B2 | 6/2007 | Eidenschink et al. | |
| 7,276,078 B2 | 10/2007 | Spenser et al. | |
| 7,276,084 B2 | 10/2007 | Yang et al. | |
| 7,316,710 B1 | 1/2008 | Cheng et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,462,191 B2 | 12/2008 | Spenser et al. | |
| 7,510,575 B2 | 3/2009 | Spenser et al. | |
| 7,563,280 B2 | 7/2009 | Anderson et al. | |
| 7,585,321 B2 | 9/2009 | Cribier | |
| 7,618,446 B2 | 11/2009 | Andersen et al. | |
| 7,618,447 B2 | 11/2009 | Case et al. | |
| 7,655,034 B2 | 2/2010 | Mitchell et al. | |
| 7,785,366 B2 | 8/2010 | Maurer et al. | |
| 7,921,678 B2* | 4/2011 | Norris | D04B 21/205 66/195 |
| 7,959,665 B2 | 6/2011 | Pienknagura | |
| 7,959,672 B2 | 6/2011 | Salahieh et al. | |
| 7,993,394 B2* | 8/2011 | Hariton | E03C 1/025 623/2.17 |
| 8,029,556 B2 | 10/2011 | Rowe | |
| 8,075,611 B2 | 12/2011 | Millwee et al. | |
| 8,128,686 B2 | 3/2012 | Paul, Jr. et al. | |
| 8,167,932 B2 | 5/2012 | Bourang et al. | |
| 8,291,570 B2 | 10/2012 | Eidenschink et al. | |
| 8,348,998 B2 | 1/2013 | Pintor et al. | |
| 8,403,983 B2* | 3/2013 | Quadri | A61F 2/2412 623/2.14 |
| 8,449,606 B2 | 5/2013 | Eliasen et al. | |
| 8,454,685 B2 | 6/2013 | Hariton et al. | |
| 8,652,203 B2 | 2/2014 | Quadri et al. | |
| 8,747,463 B2 | 6/2014 | Fogarty et al. | |
| 9,078,781 B2 | 7/2015 | Ryan et al. | |
| 9,393,110 B2 | 7/2016 | Levi et al. | |
| 9,510,946 B2* | 12/2016 | Chau | A61F 2/2436 |
| 10,179,043 B2* | 1/2019 | Cohen-Tzemach | A61F 2/2418 |
| 10,213,307 B2* | 2/2019 | Dwork | A61F 2/2469 |
| 11,628,062 B2* | 4/2023 | Levi | A61F 2/2418 623/2.14 |
| 11,654,023 B2 | 5/2023 | Zamani et al. | |
| 11,806,234 B2* | 11/2023 | Gurovich | A61F 2/2433 |
| 11,883,281 B2* | 1/2024 | Hoang | A61F 2/2409 |
| 12,064,341 B2* | 8/2024 | Hoang | A61F 2/2418 |
| 2001/0021872 A1 | 9/2001 | Bailey et al. | |
| 2002/0026094 A1 | 2/2002 | Roth | |
| 2002/0032481 A1 | 3/2002 | Gabbay | |
| 2002/0116070 A1* | 8/2002 | Amara | D04B 1/02 623/23.74 |
| 2002/0138135 A1 | 9/2002 | Duerig et al. | |
| 2002/0143390 A1 | 10/2002 | Ishii | |
| 2002/0151958 A1 | 10/2002 | Chuter | |
| 2002/0173842 A1 | 11/2002 | Buchanan | |
| 2003/0014105 A1 | 1/2003 | Cao | |
| 2003/0050694 A1 | 3/2003 | Yang et al. | |
| 2003/0078652 A1* | 4/2003 | Sutherland | A61F 2/2412 623/2.12 |
| 2003/0100939 A1 | 5/2003 | Yodfat et al. | |
| 2003/0158597 A1 | 8/2003 | Quiachon et al. | |
| 2003/0204249 A1 | 10/2003 | Letort | |
| 2003/0212454 A1 | 11/2003 | Scott et al. | |
| 2004/0024452 A1 | 2/2004 | Kruse et al. | |
| 2004/0039436 A1 | 2/2004 | Spenser et al. | |
| 2004/0078074 A1 | 4/2004 | Anderson et al. | |
| 2004/0186558 A1 | 9/2004 | Pavcnik et al. | |
| 2004/0186565 A1 | 9/2004 | Schreck | |
| 2004/0243211 A1 | 12/2004 | Colliou et al. | |
| 2004/0256759 A1 | 12/2004 | Hartley | |
| 2004/0260389 A1 | 12/2004 | Case et al. | |
| 2005/0010285 A1 | 1/2005 | Lambrecht et al. | |
| 2005/0075724 A1 | 4/2005 | Svanidze et al. | |
| 2005/0075725 A1 | 4/2005 | Rowe | |
| 2005/0075728 A1 | 4/2005 | Nguyen et al. | |
| 2005/0096736 A1 | 5/2005 | Osse et al. | |
| 2005/0096738 A1 | 5/2005 | Cali et al. | |
| 2005/0137690 A1 | 6/2005 | Salahieh et al. | |
| 2005/0188525 A1 | 9/2005 | Weber et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0004469 A1 | 1/2006 | Sokel | |
| 2006/0025857 A1 | 2/2006 | Bergheim et al. | |
| 2006/0058872 A1 | 3/2006 | Salahieh et al. | |
| 2006/0074484 A1 | 4/2006 | Huber | |
| 2006/0095025 A1 | 5/2006 | Levine et al. | |
| 2006/0108090 A1 | 5/2006 | Ederer et al. | |
| 2006/0149350 A1 | 7/2006 | Patel et al. | |
| 2006/0183383 A1 | 8/2006 | Asmus et al. | |
| 2006/0190074 A1* | 8/2006 | Hill | A61F 2/2475 623/2.18 |
| 2006/0195183 A1 | 8/2006 | Navia et al. | |
| 2006/0229719 A1 | 10/2006 | Marquez et al. | |
| 2006/0259136 A1 | 11/2006 | Nguyen et al. | |
| 2006/0259137 A1 | 11/2006 | Artof et al. | |
| 2006/0287717 A1 | 12/2006 | Rowe et al. | |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0112422 A1 | 5/2007 | Dehdashtian | |
| 2007/0142907 A1 | 6/2007 | Moaddeb et al. | |
| 2007/0162102 A1 | 7/2007 | Ryan et al. | |
| 2007/0203503 A1 | 8/2007 | Salahieh et al. | |
| 2007/0203575 A1 | 8/2007 | Forster et al. | |
| 2007/0203576 A1 | 8/2007 | Lee et al. | |
| 2007/0208550 A1 | 9/2007 | Cao et al. | |
| 2007/0213813 A1 | 9/2007 | Von Segesser et al. | |
| 2007/0233228 A1 | 10/2007 | Eberhardt et al. | |
| 2007/0260305 A1 | 11/2007 | Drews et al. | |
| 2007/0265700 A1 | 11/2007 | Eliasen et al. | |
| 2007/0270944 A1 | 11/2007 | Bergheim et al. | |
| 2008/0021546 A1 | 1/2008 | Patz et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0183271 A1 | 7/2008 | Frawley et al. | |
| 2008/0208327 A1 | 8/2008 | Rowe | |
| 2008/0243245 A1 | 10/2008 | Thambar et al. | |
| 2008/0255660 A1 | 10/2008 | Guyenot et al. | |
| 2008/0275537 A1 | 11/2008 | Limon | |

(56) References Cited

U.S. PATENT DOCUMENTS

| | | |
|---|---|---|
| 2008/0294248 A1 | 11/2008 | Yang et al. |
| 2008/0319521 A1 | 12/2008 | Norris et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0036484 A1* | 2/2010 | Hariton ............... A61F 2/2412 623/2.18 |
| 2010/0049313 A1 | 2/2010 | Alon et al. |
| 2010/0082094 A1* | 4/2010 | Quadri ............... A61F 2/2418 29/890.132 |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2010/0298927 A1 | 11/2010 | Greenberg |
| 2011/0004299 A1 | 1/2011 | Essinger et al. |
| 2011/0015729 A1 | 1/2011 | Jimenez et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0090729 A1 | 4/2013 | Gregg et al. |
| 2013/0150956 A1* | 6/2013 | Yohanan ............... A61F 2/2433 623/2.14 |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1* | 9/2014 | Schraut ............... A61F 2/2418 623/2.17 |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0303719 A1* | 10/2014 | Cox ............... A61F 2/2466 623/2.37 |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0005863 A1* | 1/2015 | Para ............... A61F 2/2418 623/1.2 |
| 2015/0073545 A1 | 3/2015 | Braido |
| 2015/0073546 A1 | 3/2015 | Braido |
| 2015/0135506 A1 | 5/2015 | White |
| 2015/0157455 A1* | 6/2015 | Hoang ............... A61M 25/0045 264/269 |
| 2015/0320556 A1* | 11/2015 | Levi ............... A61F 2/2427 29/515 |
| 2015/0327995 A1* | 11/2015 | Morin ............... A61F 2/2418 623/2.17 |
| 2016/0120646 A1 | 5/2016 | Dwork et al. |
| 2016/0354201 A1 | 12/2016 | Keogh |
| 2017/0014229 A1 | 1/2017 | Nguyen-Thien-Nhon et al. |
| 2017/0071734 A1 | 3/2017 | Delaloye et al. |
| 2018/0028310 A1 | 2/2018 | Gurovich et al. |
| 2018/0153689 A1 | 6/2018 | Maimon et al. |
| 2018/0206982 A1* | 7/2018 | Haivatov ............... A61F 2/0077 |
| 2018/0207011 A1* | 7/2018 | Rothstein ............... A61F 2/2439 |
| 2018/0325665 A1 | 11/2018 | Gurovich et al. |
| 2018/0344456 A1 | 12/2018 | Barash et al. |
| 2019/0365530 A1 | 12/2019 | Hoang et al. |
| 2022/0218468 A1 | 7/2022 | Hoang et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| EP | 3570782 A1 | 11/2019 |
| FR | 2788217 A1 | 7/2000 |
| FR | 2815844 A1 | 5/2002 |
| FR | 2903292 A1 | 1/2008 |
| GB | 1264472 A | 2/1972 |
| GB | 2056023 A | 3/1981 |
| JP | 2008538937 A | 11/2008 |
| JP | 2014534874 A | 12/2014 |
| JP | 2019503232 A | 2/2019 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 0018333 A1 | 4/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 A1 | 3/2002 |
| WO | 0228314 A2 | 4/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 A1 | 4/2005 |
| WO | 2005055883 A1 | 6/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009051682 A1 | 4/2009 |

(56) References Cited

FOREIGN PATENT DOCUMENTS

| WO | 2009053497 A1 | 4/2009 |
|---|---|---|
| WO | 2009061389 A2 | 5/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2011133787 A1 | 10/2011 |
| WO | 2012048035 A2 | 4/2012 |
| WO | 2013106585 A1 | 7/2013 |
| WO | 2014164832 A1 | 10/2014 |
| WO | 2015085218 A1 | 6/2015 |
| WO | 2015168410 A1 | 11/2015 |
| WO | 2016073189 A1 | 5/2016 |
| WO | 2016126511 A2 | 8/2016 |
| WO | 2018026865 A1 | 2/2018 |
| WO | 2018081252 A1 | 5/2018 |
| WO | 2018136971 A1 | 7/2018 |

OTHER PUBLICATIONS

Bailey, S. "Percutaneous Expandable Prosthetic Valves," Textbook of Interventional Cardiology vol. 2, 2nd Ed. pp. 1268-1276. 1994.

Cheung, Anson, et al., Transapical Transcatheter Mitral Valve-in-Valve Implantation in a Human, Annals of Thoracic Surgery, 87:e 18-20 (2009).

H.R. Andersen "History of Percutaneous Aortic Valve Prosthesis," Herz No. 34. pp. 343-346. 2009.

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Uchida, "Modifications of Gianturco Expandable Wire Stents," American Journal of Roentgenology, vol. 150. pp. 1185-1187. 1986.

Walther, Thomas et al., "Trans-catheter valve-in-valve implantation: in vitro hydrodynamic performance of the Sapien + cloth transcatheter heart valve in the Carpentier-Edwards Perimount valves" European Journal of Cardio-Thoracic Surgery, vol. 40, No. 1120, Apr. 3, 2011.

Wheatley, "Valve Prostheses," Operative Surgery, 4th ed. pp. 415-424. 1986.

\* cited by examiner

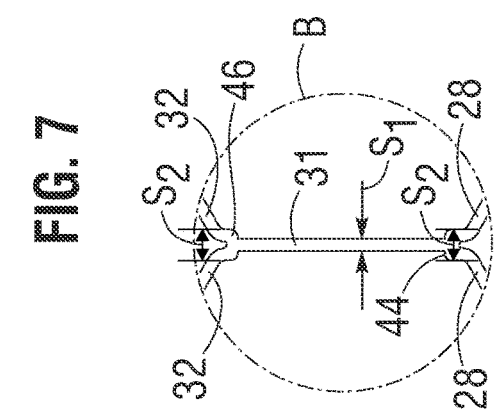
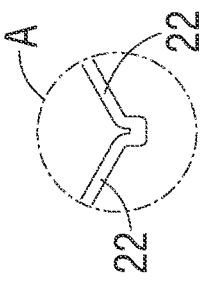
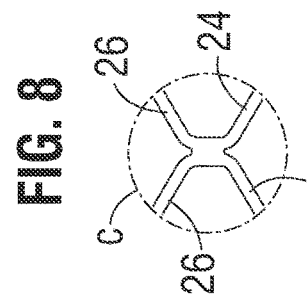
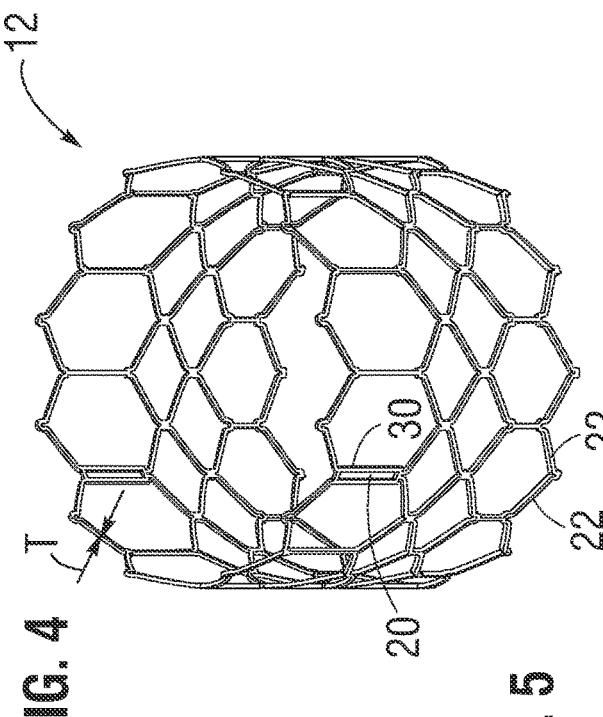
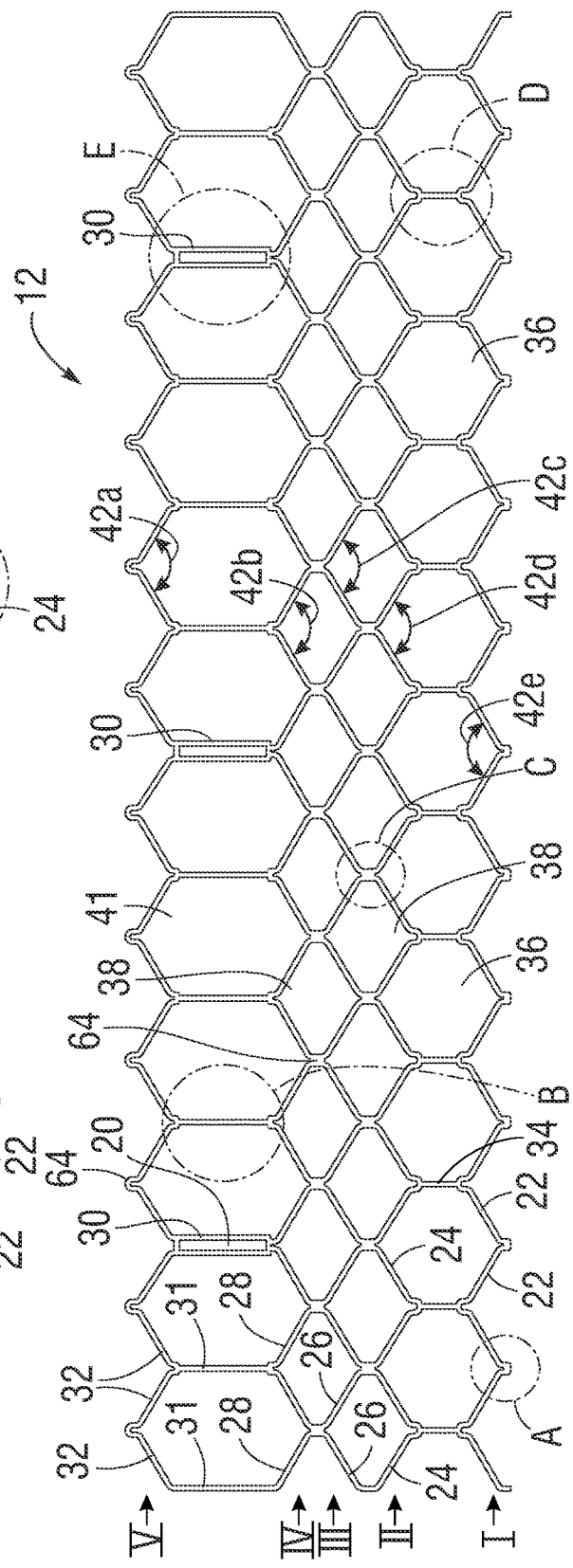

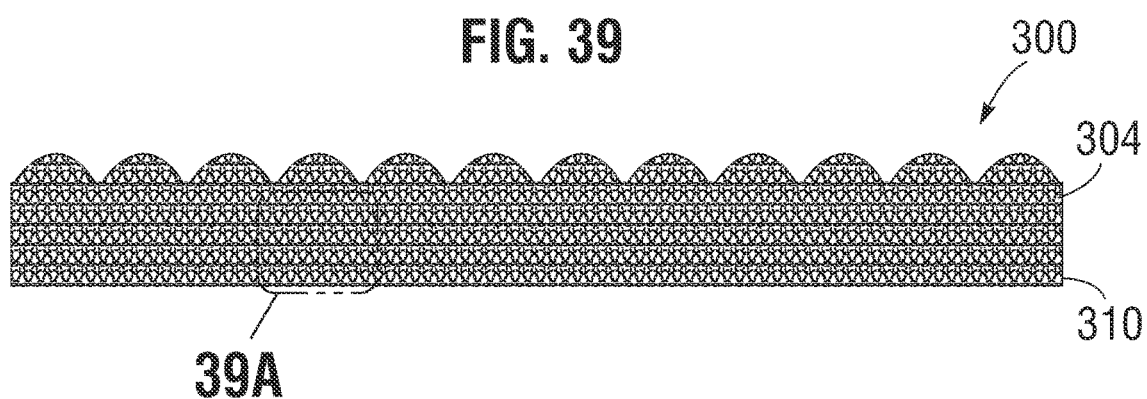
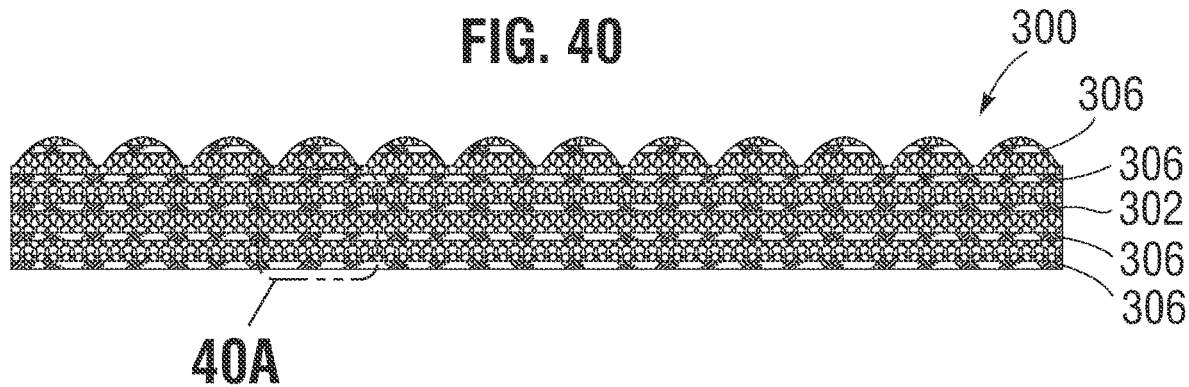

SEALING MEMBER FOR PROSTHETIC HEART VALVE

CROSS-REFERENCE TO RELATED APPLICATIONS

This application is a continuation of U.S. patent application Ser. No. 17/708,428, filed Mar. 30, 2022, now U.S. Pat. No. 11,883,281, which is a continuation of U.S. patent application Ser. No. 16/120,112, filed Aug. 31, 2018, which is continuation-in-part of U.S. patent application Ser. No. 15/991,325, filed on May 29, 2018, now abandoned, which claims the benefit of U.S. Patent Application No. 62/513,348, filed on May 31, 2017. The entire contents of the foregoing applications are incorporated herein by reference.

FIELD

The present disclosure relates to implantable, expandable prosthetic devices and to methods and apparatuses for such prosthetic devices.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans. Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For example, collapsible transcatheter prosthetic heart valves can be crimped to a compressed state and percutaneously introduced in the compressed state on a catheter and expanded to a functional size at the desired position by balloon inflation or by utilization of a self-expanding frame or stent.

A prosthetic valve for use in such a procedure can include a radially collapsible and expandable frame to which leaflets of the prosthetic valve can be coupled. For example, U.S. Pat. Nos. 6,730,118, 7,393,360, 7,510,575, and 7,993,394, which are incorporated herein by reference, describe exemplary collapsible transcatheter heart valves (THVs).

A challenge in catheter-implanted prosthetic valves is the process of crimping such a prosthetic valve to a profile suitable for percutaneous delivery to a subject. Another challenge is the control of paravalvular leakage around the valve, which can occur for a period of time following initial implantation.

Paravalvular leakage has been a known problem since the first replacement valves were introduced. The earliest prosthetic heart valves, those that were implanted surgically, included a circumferential sewing ring that was adapted to extend into spaces in the tissue surrounding the implanted prosthesis to prevent paravalvular leaking. For example, U.S. Pat. No. 3,365,728 describes a prosthetic heart valve for surgical implantation that includes a rubber "cushion ring" that conforms to irregularities of the tissue to form an effective seal between the valve and the surrounding tissue. From there, vascular stents or stent grafts were developed that could be implanted by non-surgical catheterization techniques. These stents included a fabric covering that allowed the stent to be used to isolate and reinforce the wall of a blood vessel from the lumen of the vessel. These fabric coverings served essentially the same purpose on stents as did the sealing rings on surgical heart valves—they reduced the risk of blood leaking between the prosthesis and the surrounding tissue. Multiple graft designs were developed that further enhanced the external seal to prevent blood from flowing between the graft and surrounding cardiovascular tissue. For example, U.S. Pat. No. 6,015,431 to Thornton discloses a seal secured to the outer surface of a stent that is adapted to occlude leakage flow externally around the stent wall between the outer surface and the endolumenal wall when the stent is deployed, by conforming to the irregular surface of the surrounding tissue. U.S. Patent Publication 2003/0236567 to Elliot similarly discloses a tubular prosthesis having a stent and one or more fabric "skirts" to seal against endoleaks. U.S. Patent Publication 2004/0082989 to Cook et al. also recognized the potential for endoleaks, and describes a stent graft having a cuff portion that has an external sealing zone that extends around the body of the stent to prevent leakage. The cuff portion could be folded over to create a pocket that collects any blood passing around the leading edge of the graft to prevent an endoleak.

Building on this technology, in the late 1980's, the first permanent bioprosthetic heart valve was implanted using transcatheter techniques. U.S. Pat. No. 5,411,552 to Andersen describes a THV comprising a valve mounted within a collapsible and expandable stent structure. Certain embodiments have additional graft material used along the external and internal surface of the THV. As with stent grafts, the covers proposed to be used with THVs were designed to conform to the surface of the surrounding tissue to prevent paravalvular leaks.

Like with stents, "cuffs" or other outer seals were used on THVs. U.S. Pat. No. 5,855,601 to Bessler describes a self-expanding THV having a cuff portion extending along the outside of the stent. Upon collapse of the stent for delivery, the outer seal collapses to form pleats, then expands with the stent to provide a seal between the THV and the surrounding tissue.

Thereafter, a different THV design was described by Pavcnik in U.S. Patent Application Publication 2001/0039450. The enhanced sealing structure of Pavcnik is in the form of corner "flaps" or "pockets" secured to the stent at the edges of each "flap" or "pocket" and positioned at discrete locations around the prosthesis. The corner flap was designed to catch retrograde blood flow to provide a better seal between the THV and the vessel wall, as well as to provide an improved substrate for ingrowth of native tissue.

Thus, fabric and other materials used to cover and seal both internal and external surfaces of THVs and other endovascular prostheses such as stents and stent grafts are well known. These covers can be made with low-porosity woven fabric materials, as described, for example, by U.S. Pat. No. 5,957,949 to Leonhardt et al., which describes a valve stent having an outer cover that can conform to the living tissue surrounding it upon implantation to help prevent blood leakage.

Several more recent THV designs include a THV with an outer covering. U.S. Pat. No. 7,510,575 to Spenser discloses a THV having a cuff portion wrapped around the outer surface of the support stent at the inlet. The cuff portion is rolled up over the edge of the frame so as to provide a "sleeve-like" portion at the inlet to form a cuff over the inlet that helps prevent blood leakage. U.S. Pat. No. 8,002,825 to Letac and Cribier describes an internal cover that extends from the base of the valve to the lower end of the stent and then up the external wall of the stent so as to form an external cover. The single-piece cover could be made with any of the materials disclosed for making the valve structure, which include fabric (e.g., Dacron), biological material (e.g., pericardium), or other synthetic materials (e.g., polyethylene).

While covers used on the external surface of an endovascular prosthesis to prevent paravalvular leaking are well known, there remains a need for improved coverings that provide enhanced sealing while still providing a small profile suitable for percutaneous delivery to a patient.

SUMMARY

Embodiments of a radially collapsible and expandable prosthetic valve are disclosed herein that include an improved outer skirt for reducing perivalvular leakage, as well as related methods and apparatuses including such prosthetic valves. In several embodiments, the disclosed prosthetic valves are configured as replacement heart valves for implantation into a subject.

In one representative embodiment, a prosthetic heart valve comprises an annular frame that comprises an inflow end and an outflow end and is radially compressible and expandable between a radially compressed configuration and a radially expanded configuration. The prosthetic heart valve further includes a leaflet structure positioned within the frame and secured thereto, and an outer sealing member mounted outside of the frame and adapted to seal against surrounding tissue when the prosthetic heart valve is implanted within a native heart valve annulus of a patient. The sealing member can comprise a mesh layer and pile layer comprising a plurality of pile yarns extending outwardly from the mesh layer.

In some embodiments, the mesh layer comprises a knit or woven fabric.

In some embodiments, the pile yarns are arranged to form a looped pile.

In some embodiments, the pile yarns are cut to form a cut pile.

In some embodiments, the height of the pile yarns varies along a height and/or a circumference of the outer skirt.

In some embodiments, the pile yarns comprise a first group of yarns along an upstream portion of the outer skirt and a second group of yarns along a downstream portion of the outer skirt, wherein the yarns of the first group have a height that is less than a height of the yarns of the second group.

In some embodiments, the pile yarns comprise a first group of yarns along an upstream portion of the outer skirt and a second group of yarns along a downstream portion of the outer skirt, wherein the yarns of the first group have a height that is greater than a height of the yarns of the second group.

In some embodiments, the pile yarns comprise a first group of yarns along an upstream portion of the outer skirt, a second group of yarns along a downstream portion of the outer skirt, and a third group of yarns between the first and second group of yarns, wherein the yarns of the first and second groups have a height that is greater than a height of the yarns of the third group.

In some embodiments, the prosthetic heart valve further comprises an inner skirt mounted on an inner surface of the frame, the inner skirt having an inflow end portion that is secured to an inflow end portion of the outer sealing member.

In some embodiments, the inflow end portion of the inner skirt is wrapped around an inflow end of the frame and overlaps the inflow end portion of the outer sealing member on the outside of the frame.

In some embodiments, the mesh layer comprises a first mesh layer and the outer sealing member further comprises a second mesh layer disposed radially outside of the pile layer.

In some embodiments, the outer sealing member is configured to stretch axially when the frame is radially compressed to the radially compressed state.

In some embodiments, the mesh layer comprises warp yarns and weft yarns woven with the warp yarns, and the pile layer comprises the warp yarns or the weft yarns of the mesh layer that are woven or knitted to form the pile yarns.

In some embodiments, the mesh layer comprises a woven fabric layer and the pile layer comprises a separate pile layer that is stitched to the woven fabric layer.

In some embodiment, the mesh layer has a first height extending axially along the frame and the pile layer comprises a second height extending axially along the frame, wherein the first height is greater than the second height.

In some embodiment, the mesh layer extends closer to the outflow end of the frame than the pile layer.

In another representative embodiment, a prosthetic heart valve comprises an annular frame that comprises an inflow end and an outflow end and is radially compressible and expandable between a radially compressed configuration and a radially expanded configuration. The prosthetic heart valve further comprises a leaflet structure positioned within the frame and secured thereto, an outer sealing member mounted outside of the frame and adapted to seal against surrounding tissue when the prosthetic heart valve is implanted within a native heart valve annulus of a patient. The sealing member can comprise a fabric having a variable thickness.

In some embodiments, the thickness of the fabric layer varies along a height and/or a circumference of the outer sealing member.

In some embodiments, the fabric comprises a plush fabric.

In some embodiments, the fabric comprises a plurality of pile yarns and the height of the pile yarns varies along a height and/or a circumference of the outer skirt.

In some embodiments, the pile yarns comprise a first group of yarns along an upstream portion of the outer skirt and a second group of yarns along a downstream portion of the outer skirt, wherein the yarns of the first group have a height that is less than a height of the yarns of the second group.

In some embodiments, the pile yarns comprise a first group of yarns along an upstream portion of the outer skirt and a second group of yarns along a downstream portion of the outer skirt, wherein the yarns of the first group have a height that is greater than a height of the yarns of the second group.

In some embodiments, the pile yarns comprise a first group of yarns along an upstream portion of the outer skirt, a second group of yarns along a downstream portion of the outer skirt, and a third group of yarns between the first and second group of yarns, wherein the yarns of the first and second groups have a height that is greater than a height of the yarns of the third group.

In another representative embodiment, a prosthetic heart valve comprises an annular frame that comprises an inflow end and an outflow end and is radially compressible and expandable between a radially compressed configuration and a radially expanded configuration. The prosthetic heart valve further comprises a leaflet structure positioned within the frame and secured thereto, an outer sealing member mounted outside of the frame and adapted to seal against surrounding tissue when the prosthetic heart valve is implanted within a native heart valve annulus of a patient. The sealing member can comprise a pile fabric comprising a plurality of pile yarns, wherein the density of the pile yarns varies in an axial direction and/or a circumferential direction along the sealing member.

In some embodiments, the pile yarns are arranged in circumferentially extending rows of pile yarns and the density of the pile yarns varies from row to row.

In some embodiments, the pile yarns are arranged in axially extending rows pile yarns and the density of the pile yarns varies from row to row.

In some embodiments, the sealing member comprises a mesh layer and a pile layer comprising the pile yarns. In some embodiments, the weave density of the mesh layer varies in an axial direction and/or a circumferential direction along the sealing member. In some embodiments, the mesh layer comprises one or more rows of higher-density mesh portions and one or more rows of lower-density mesh portions. The one or more rows of higher-density mesh portions and the one or more rows of lower-density mesh portions can be circumferentially extending rows and/or axially extending rows.

In another representative embodiment, a prosthetic heart valve comprises an annular frame that comprises an inflow end and an outflow end and is radially compressible and expandable between a radially compressed configuration and a radially expanded configuration. The prosthetic heart valve further comprises a leaflet structure positioned within the frame and secured thereto, an outer sealing member mounted outside of the frame and adapted to seal against surrounding tissue when the prosthetic heart valve is implanted within a native heart valve annulus of a patient. The sealing member comprises a textile formed from a plurality fibers arranged in a plurality of axially extending rows of higher stitch density interspersed between a plurality of axially extending rows of lower stitch density. The sealing member is configured to stretch axially between a first, substantially relaxed, axially foreshortened configuration when the frame is the radially expanded configuration and a second, axially elongated configuration when the frame is in the radially compressed configuration.

In some embodiments, each of the rows of higher stitch density can extend in an undulating pattern when the sealing member is in the axially foreshortened configuration. When the sealing member is in the axially elongated configuration, the rows of higher stitch density move from the undulating pattern toward a straightened pattern.

In another representative embodiment, a prosthetic heart valve comprises an annular frame that comprises an inflow end and an outflow end and is radially compressible and expandable between a radially compressed configuration and a radially expanded configuration. The prosthetic heart valve further comprises a leaflet structure positioned within the frame and secured thereto, an outer sealing member mounted outside of the frame and adapted to seal against surrounding tissue when the prosthetic heart valve is implanted within a native heart valve annulus of a patient. The sealing member comprises a fabric comprising a plurality of axially extending filaments and a plurality of circumferentially extending filaments. The sealing member is configured to stretch axially when the frame is radially compressed from the radially expanded configuration to the radially compressed configuration. The axially extending filaments move from a deformed or twisted state when the frame is in the radially expanded configuration to a less deformed or less twisted state when the frame is in the radially compressed configuration.

In some embodiments, the axially extending filaments are heat set in the deformed or twisted state.

In some embodiments, the thickness of the sealing member decreases when the axially extending filaments move from the deformed or twisted state to the less deformed or twisted state.

BRIEF DESCRIPTION OF THE DRAWINGS

FIGS. 4-10 show an exemplary frame of the prosthetic heart valve of FIG. 1.

FIG. 39 is a flattened view of the outer surface of an outer sealing member for a prosthetic heart valve, according to another embodiment.

FIG. 40 is a flattened view of the inner surface of the sealing member of FIG. 39.

DETAILED DESCRIPTION

Figure 1:
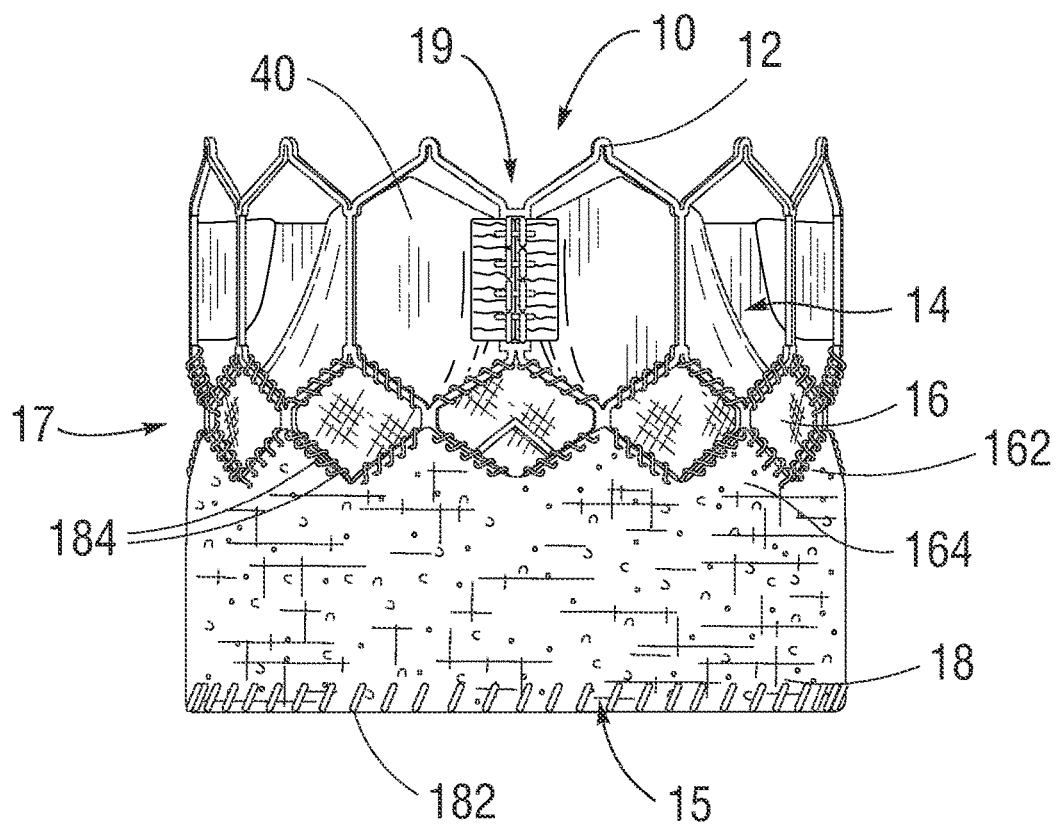
FIG. 1 is a perspective view of a prosthetic heart valve, according to one embodiment.

FIG. 1 shows a prosthetic heart valve 10, according to one embodiment. The illustrated prosthetic valve is adapted to be implanted in the native aortic annulus, although in other embodiments it can be adapted to be implanted in the other native annuluses of the heart (e.g., the pulmonary, mitral, and tricuspid valves). The prosthetic valve can also be adapted to be implanted in other tubular organs or passageways in the body. The prosthetic valve 10 can have four main components: a stent or frame 12, a valvular structure 14, an inner skirt 16, and a perivalvular outer sealing member or outer skirt 18. The prosthetic valve 10 can have an inflow end portion 15, an intermediate portion 17, and an outflow end portion 19.

The valvular structure 14 can comprise three leaflets 40 (FIG. 17), collectively forming a leaflet structure, which can be arranged to collapse in a tricuspid arrangement. The lower edge of leaflet structure 14 desirably has an undulating, curved scalloped shape (suture line 154 shown in FIG. 20 tracks the scalloped shape of the leaflet structure). By forming the leaflets with this scalloped geometry, stresses on the leaflets are reduced, which in turn improves durability of the prosthetic valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the prosthetic valve. The leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The bare frame 12 is shown in FIG. 4. The frame 12 can be formed with a plurality of circumferentially spaced slots, or commissure windows, 20 (three in the illustrated embodiment) that are adapted to mount the commissures of the valvular structure 14 to the frame, as described in greater detail below. The frame 12 can be made of any of various suitable plastically-expandable materials (e.g., stainless steel, etc.) or self-expanding materials (e.g., nickel titanium alloy (NiTi), such as nitinol) as known in the art. When constructed of a plastically-expandable material, the frame 12 (and thus the prosthetic valve 10) can be crimped to a radially collapsed configuration on a delivery catheter and then expanded inside a patient by an inflatable balloon or equivalent expansion mechanism. When constructed of a self-expandable material, the frame 12 (and thus the prosthetic valve 10) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size.

Suitable plastically-expandable materials that can be used to form the frame 12 include, without limitation, stainless steel, a biocompatible, high-strength alloys (e.g., a cobalt-chromium or a nickel-cobalt-chromium alloys), polymers, or combinations thereof. In particular embodiments, frame 12 is made of a nickel-cobalt-chromium-molybdenum alloy, such as MP35N® alloy (SPS Technologies, Jenkintown, Pennsylvania), which is equivalent to UNS R30035 alloy (covered by ASTM F562-02). MP35N® alloy/UNS R30035 alloy comprises 35% nickel, 35% cobalt, 20% chromium, and 10% molybdenum, by weight. It has been found that the use of MP35N® alloy to form frame 12 provides superior structural results over stainless steel. In particular, when MP35N® alloy is used as the frame material, less material is needed to achieve the same or better performance in radial and crush force resistance, fatigue resistances, and corrosion resistance. Moreover, since less material is required, the crimped profile of the frame can be reduced, thereby providing a lower profile prosthetic valve assembly for percutaneous delivery to the treatment location in the body.

Referring to FIGS. 4 and 5, the frame 12 in the illustrated embodiment comprises a first, lower row I of angled struts 22 arranged end-to-end and extending circumferentially at the inflow end of the frame; a second row II of circumferentially extending, angled struts 24; a third row III of circumferentially extending, angled struts 26; a fourth row IV of circumferentially extending, angled struts 28; and a fifth row V of circumferentially extending, angled struts 32 at the outflow end of the frame. A plurality of substantially straight axially extending struts 34 can be used to interconnect the struts 22 of the first row I with the struts 24 of the second row II. The fifth row V of angled struts 32 are connected to the fourth row IV of angled struts 28 by a plurality of axially extending window frame portions 30 (which define the commissure windows 20) and a plurality of axially extending struts 31. Each axial strut 31 and each frame portion 30 extends from a location defined by the convergence of the lower ends of two angled struts 32 to another location defined by the convergence of the upper ends of two angled struts 28. FIGS. 6, 7, 8, 9, and 10 are enlarged views of the portions of the frame 12 identified by letters A, B, C, D, and E, respectively, in FIG. 5.

Each commissure window frame portion 30 mounts a respective commissure of the leaflet structure 14. As can be seen each frame portion 30 is secured at its upper and lower ends to the adjacent rows of struts to provide a robust configuration that enhances fatigue resistance under cyclic loading of the prosthetic valve compared to known, cantilevered struts for supporting the commissures of the leaflet structure. This configuration enables a reduction in the frame wall thickness to achieve a smaller crimped diameter of the prosthetic valve. In particular embodiments, the thickness T of the frame 12 (FIG. 4) measured between the inner diameter and outer diameter is about 0.48 mm or less.

The struts and frame portions of the frame collectively define a plurality of open cells of the frame. At the inflow end of the frame 12, struts 22, struts 24, and struts 34 define a lower row of cells defining openings 36. The second, third, and fourth rows of struts 24, 26, and 28 define two intermediate rows of cells defining openings 38. The fourth and fifth rows of struts 28 and 32, along with frame portions 30 and struts 31, define an upper row of cells defining openings 40. The openings 41 are relatively large and are sized to allow portions of the leaflet structure 14 to protrude, or bulge, into and/or through the openings 40 when the frame 12 is crimped in order to minimize the crimping profile.

As best shown in FIG. 7, the lower end of the strut 31 is connected to two struts 28 at a node or junction 44, and the upper end of the strut 31 is connected to two struts 32 at a node or junction 46. The strut 31 can have a thickness S1 that is less than the thicknesses S2 of the junctions 44, 46. The junctions 44, 46, along with junctions 64, prevent full closure of openings 40. The geometry of the struts 31, and junctions 44, 46, and 64 assists in creating enough space in openings 41 in the collapsed configuration to allow portions of the prosthetic leaflets to protrude or bulge outwardly through openings. This allows the prosthetic valve to be crimped to a relatively smaller diameter than if all of the leaflet material were constrained within the crimped frame.

The frame 12 is configured to reduce, to prevent, or to minimize possible over-expansion of the prosthetic valve at a predetermined balloon pressure, especially at the outflow end portion of the frame, which supports the leaflet structure 14. In one aspect, the frame is configured to have relatively larger angles 42a, 42b, 42c, 42d, 42e between struts, as shown in FIG. 5. The larger the angle, the greater the force required to open (expand) the frame. As such, the angles between the struts of the frame can be selected to limit radial expansion of the frame at a given opening pressure (e.g., inflation pressure of the balloon). In particular embodiments, these angles are at least 110 degrees or greater when the frame is expanded to its functional size, and even more particularly these angles are up to about 120 degrees when the frame is expanded to its functional size.

In addition, the inflow and outflow ends of a frame generally tend to over-expand more so than the middle portion of the frame due to the "dog-boning" effect of the balloon used to expand the prosthetic valve. To protect against over-expansion of the leaflet structure 14, the leaflet structure desirably is secured to the frame 12 below the upper row of struts 32, as best shown in FIG. 1. Thus, in the event that the outflow end of the frame is over-expanded, the leaflet structure is positioned at a level below where over-expansion is likely to occur, thereby protecting the leaflet structure from over-expansion.

In a known prosthetic valve construction, portions of the leaflets can protrude longitudinally beyond the outflow end of the frame when the prosthetic valve is crimped if the leaflets are mounted too close to the distal end of the frame. If the delivery catheter on which the crimped prosthetic valve is mounted includes a pushing mechanism or stop member that pushes against or abuts the outflow end of the prosthetic valve (for example, to maintain the position of the crimped prosthetic valve on the delivery catheter), the pushing member or stop member can damage the portions of the exposed leaflets that extend beyond the outflow end of the frame. Another benefit of mounting the leaflets at a location spaced away from the outflow end of the frame is that when the prosthetic valve is crimped on a delivery catheter, the outflow end of the frame 12 rather than the leaflets 40 is the proximal-most component of the prosthetic valve 10. As such, if the delivery catheter includes a pushing mechanism or stop member that pushes against or abuts the outflow end of the prosthetic valve, the pushing mechanism or stop member contacts the outflow end of the frame, and not leaflets 40, so as to avoid damage to the leaflets.

Also, as can be seen in FIG. 5, the openings 36 of the lowermost row of openings in the frame are relatively larger than the openings 38 of the two intermediate rows of openings. This allows the frame, when crimped, to assume an overall tapered shape that tapers from a maximum diameter at the outflow end of the prosthetic valve to a minimum diameter at the inflow end of the prosthetic valve. When crimped, the frame 12 has a reduced diameter region extending along a portion of the frame adjacent the inflow end of the frame that generally corresponds to the region of the frame covered by the outer skirt 18. In some embodiments, the reduced diameter region is reduced compared to the diameter of the upper portion of the frame (which is not covered by the outer skirt) such that the outer skirt 18 does not increase the overall crimp profile of the prosthetic valve. When the prosthetic valve is deployed, the frame can expand to the generally cylindrical shape shown in FIG. 4. In one example, the frame of a 26-mm prosthetic valve, when crimped, had a first diameter of 14 French at the outflow end of the prosthetic valve and a second diameter of 12 French at the inflow end of the prosthetic valve.

The main functions of the inner skirt 16 are to assist in securing the valvular structure 14 to the frame 12 and to assist in forming a good seal between the prosthetic valve and the native annulus by blocking the flow of blood through the open cells of the frame 12 below the lower edge of the leaflets. The inner skirt 16 desirably comprises a tough, tear resistant material such as polyethylene terephthalate (PET), although various other synthetic materials or natural materials (e.g., pericardial tissue) can be used. The thickness of the skirt desirably is less than about 0.15 mm (about 6 mil), and desirably less than about 0.1 mm (about 4 mil), and even more desirably about 0.05 mm (about 2 mil). In particular embodiments, the skirt 16 can have a variable thickness, for example, the skirt can be thicker at at least one of its edges than at its center. In one implementation, the skirt 16 can comprise a PET skirt having a thickness of about 0.07 mm at its edges and about 0.06 mm at its center. The thinner skirt can provide for better crimping performances while still providing good perivalvular sealing.

Figure 19:
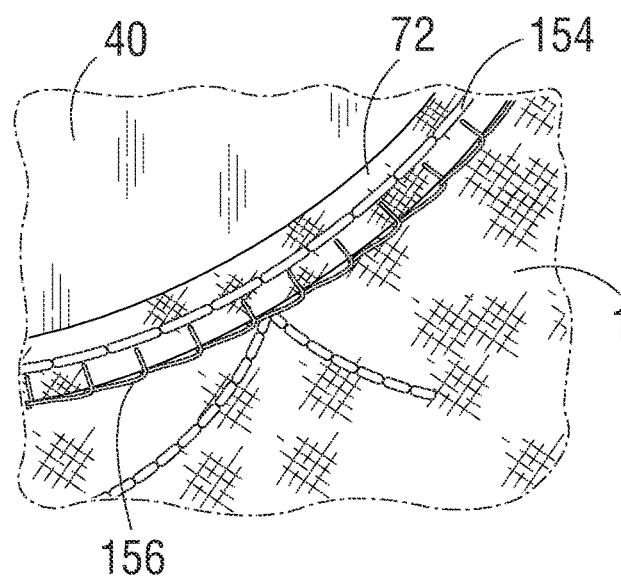
FIGS. 19-20 show the assembly of the leaflet structure with the inner skirt along a lower edge of the leaflets.
Figure 20:
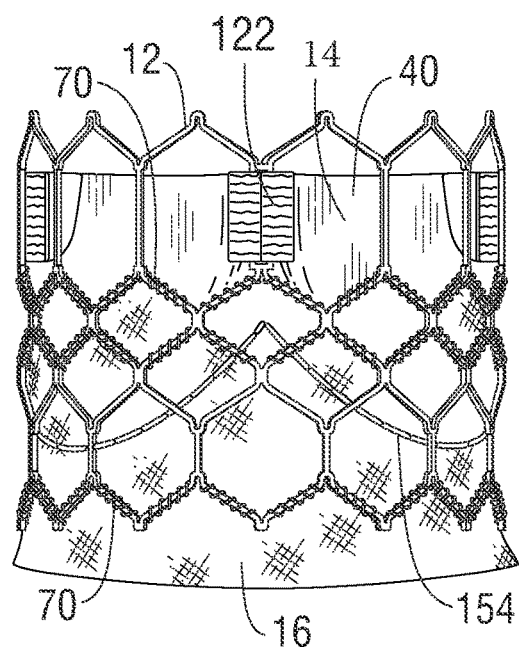

The inner skirt 16 can be secured to the inside of frame 12 via sutures 70, as shown in FIG. 20. Valvular structure 14 can be attached to the skirt via one or more reinforcing strips 72 (which collectively can form a sleeve), for example thin, PET reinforcing strips, discussed below, which enables a secure suturing and protects the pericardial tissue of the leaflet structure from tears. Valvular structure 14 can be sandwiched between skirt 16 and the thin PET strips 72 as shown in FIG. 19. Sutures 154, which secure the PET strip and the leaflet structure 14 to skirt 16, can be any suitable suture, such as Ethibond Excel® PET suture (Johnson & Johnson, New Brunswick, New Jersey). Sutures 154 desirably track the curvature of the bottom edge of leaflet structure 14, as described in more detail below.

Known fabric skirts may comprise a weave of warp and weft fibers that extend perpendicularly to each other and with one set of the fibers extending longitudinally between the upper and lower edges of the skirt. When the metal frame to which the fabric skirt is secured is radially compressed, the overall axial length of the frame increases. Unfortunately, a fabric skirt with limited elasticity cannot elongate along with the frame and therefore tends to deform the struts of the frame and to prevent uniform crimping.

Figure 12:
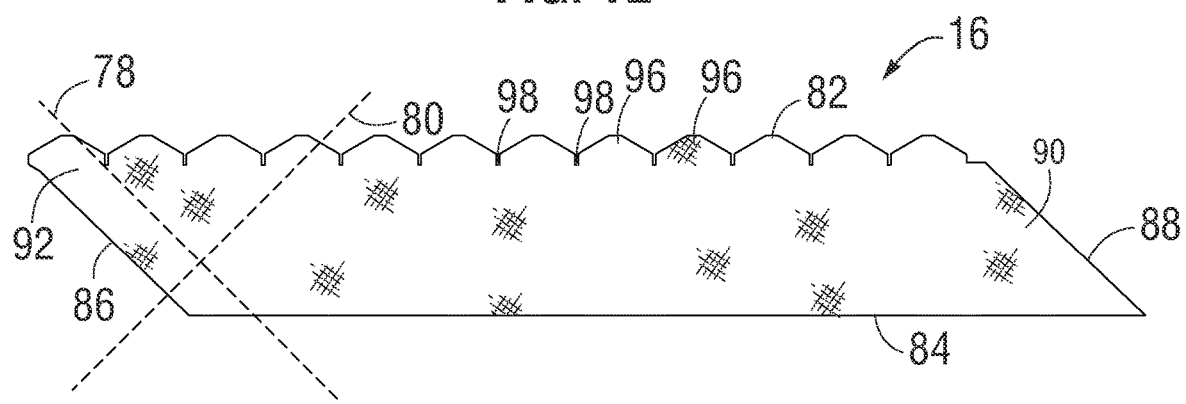

Referring to FIG. 12, in contrast to known fabric skirts, the skirt 16 desirably is woven from a first set of fibers, or yarns or strands, 78 and a second set of fibers, or yarns or strands, 80, both of which are non-perpendicular to the upper edge 82 and the lower edge 84 of the skirt. In particular embodiments, the first set of fibers 78 and the second set of fibers 80 extend at angles of about 45 degrees relative to the upper and lower edges 82, 84. Alternatively, the first set of fibers 78 and the second set of fibers 80 extend at angles other than about 45 degrees relative to the upper and lower edges 82, 84, e.g., at angles of 15 and 75 degrees, respectively, or 30 and 60 degrees, respectively, relative to the upper and lower edges 82, 84. For example, the skirt 16 can be formed by weaving the fibers at 45 degree angles relative to the upper and lower edges of the fabric. Alternatively, the skirt 16 can be diagonally cut (cut on a bias) from a vertically woven fabric (where the fibers extend perpendicularly to the edges of the material) such that the fibers extend at 45 degree angles relative to the cut upper and lower edges of the skirt. As further shown in FIG. 12, the opposing short edges 86, 88 of the skirt desirably are non-perpendicular to the upper and lower edges 82, 84. For example, the short edges 86, 88 desirably extend at angles of about 45 degrees relative to the upper and lower edges and therefore are aligned with the first set of fibers 78. Therefore the overall general shape of the skirt is that of a rhomboid or parallelogram.

Figure 13:
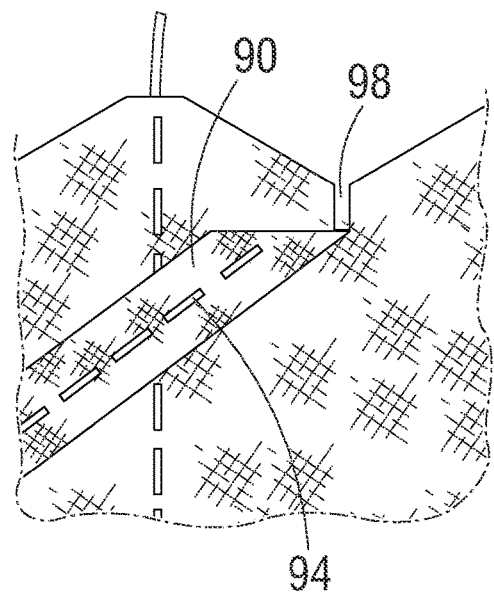
FIGS. 13-15 show the assembly of the inner skirt of FIG. 11 with the frame of FIG. 4.
Figure 14:
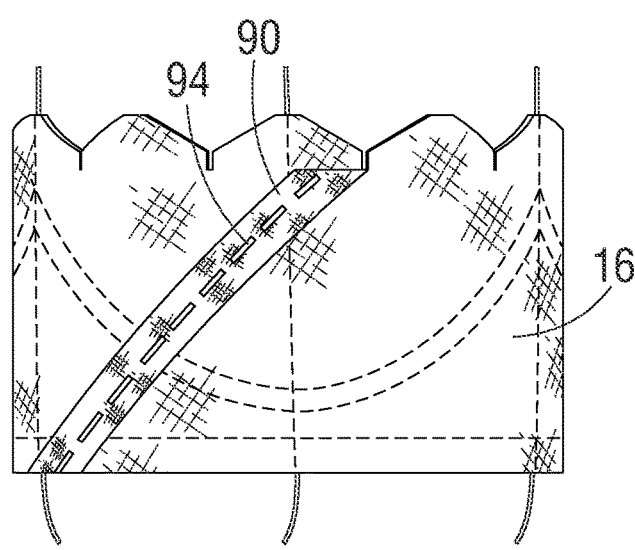
Figure 15:
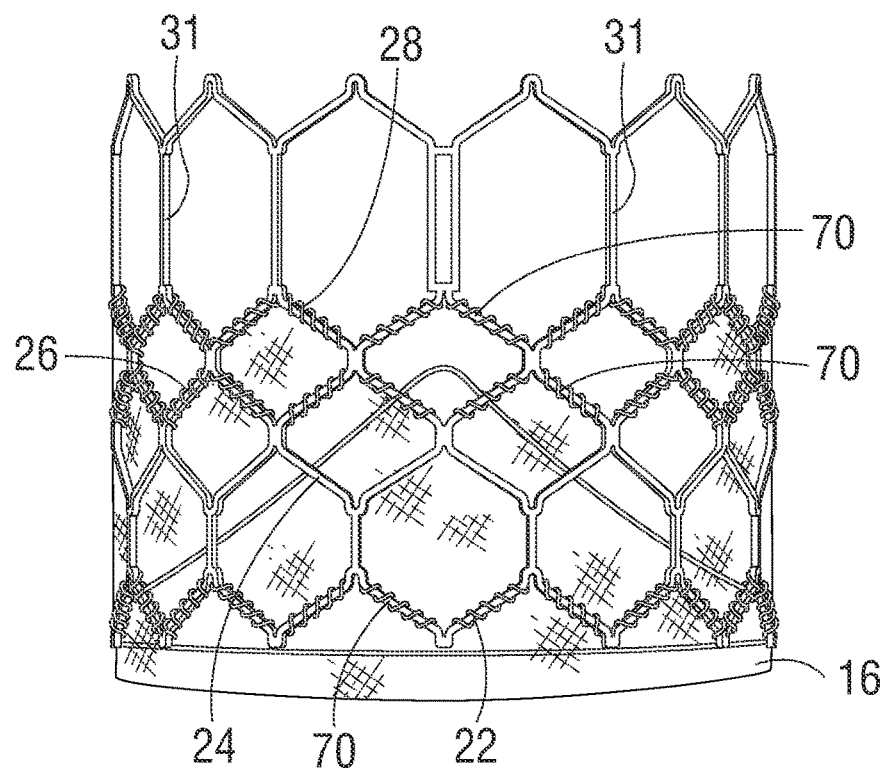

FIGS. 13 and 14 show the inner skirt 16 after opposing short edge portions 90, 92 have been sewn together to form the annular shape of the skirt. As shown, the edge portion 90 can be placed in an overlapping relationship relative to the opposite edge portion 92, and the two edge portions can be sewn together with a diagonally extending suture line 94 that is parallel to short edges 86, 88. The upper edge portion of the inner skirt 16 can be formed with a plurality of projections 96 that define an undulating shape that generally follows the shape or contour of the fourth row of struts 28 immediately adjacent the lower ends of axial struts 31. In this manner, as best shown in FIG. 15, the upper edge of the inner skirt 16 can be tightly secured to struts 28 with sutures 70. The inner skirt 16 can also be formed with slits 98 to facilitate attachment of the skirt to the frame. Slits 98 are dimensioned so as to allow an upper edge portion of the inner skirt 16 to be partially wrapped around struts 28 and to reduce stresses in the skirt during the attachment procedure. For example, in the illustrated embodiment, the inner skirt 16 is placed on the inside of frame 12 and an upper edge portion of the skirt is wrapped around the upper surfaces of struts 28 and secured in place with sutures 70. Wrapping the upper edge portion of the inner skirt 16 around struts 28 in this manner provides for a stronger and more durable attachment of the skirt to the frame. The inner skirt 16 can also be secured to the first, second, and/or third rows of struts 22, 24, and 26, respectively, with sutures 70.

Due to the angled orientation of the fibers relative to the upper and lower edges, the skirt can undergo greater elongation in the axial direction (i.e., in a direction from the upper edge 82 to the lower edge 84). Thus, when the metal frame 12 is crimped, the inner skirt 16 can elongate in the axial direction along with the frame and therefore provide a more uniform and predictable crimping profile. Each cell of the metal frame in the illustrated embodiment includes at least four angled struts that rotate towards the axial direction on crimping (e.g., the angled struts become more aligned with the length of the frame). The angled struts of each cell function as a mechanism for rotating the fibers of the skirt in the same direction of the struts, allowing the skirt to elongate along the length of the struts. This allows for greater elongation of the skirt and avoids undesirable deformation of the struts when the prosthetic valve is crimped.

In addition, the spacing between the woven fibers or yarns can be increased to facilitate elongation of the skirt in the axial direction. For example, for a PET inner skirt 16 formed from 20-denier yarn, the yarn density can be about 15% to about 30% lower than in a typical PET skirt. In some examples, the yarn spacing of the inner skirt 16 can be from about 60 yarns per cm (about 155 yarns per inch) to about 70 yarns per cm (about 180 yarns per inch), such as about 63 yarns per cm (about 160 yarns per inch), whereas in a typical PET skirt the yarn spacing can be from about 85 yarns per cm (about 217 yarns per inch) to about 97 yarns per cm (about 247 yarns per inch). The oblique edges 86, 88 promote a uniform and even distribution of the fabric material along inner circumference of the frame during crimping so as to reduce or minimize bunching of the fabric to facilitate uniform crimping to the smallest possible diameter. Additionally, cutting diagonal sutures in a vertical manner may leave loose fringes along the cut edges. The oblique edges 86, 88 help minimize this from occurring. Compared to the construction of a typical skirt (fibers running perpendicularly to the upper and lower edges of the skirt), the construction of the inner skirt 16 avoids undesirable deformation of the frame struts and provides more uniform crimping of the frame.

In alternative embodiments, the skirt can be formed from woven elastic fibers that can stretch in the axial direction during crimping of the prosthetic valve. The warp and weft fibers can run perpendicularly and parallel to the upper and lower edges of the skirt, or alternatively, they can extend at angles between 0 and 90 degrees relative to the upper and lower edges of the skirt, as described above.

The inner skirt 16 can be sutured to the frame 12 at locations away from the suture line 154 so that the skirt can be more pliable in that area. This configuration can avoid stress concentrations at the suture line 154, which attaches the lower edges of the leaflets to the inner skirt 16.

As noted above, the leaflet structure 14 in the illustrated embodiment includes three flexible leaflets 40 (although a greater or a smaller number of leaflets can be used). Additional information regarding the leaflets, as well as additional information regarding skirt material, can be found, for example, in U.S. patent application Ser. No. 14/704,861, filed May 5, 2015, which is incorporated by reference in its entirety.

Figure 16:
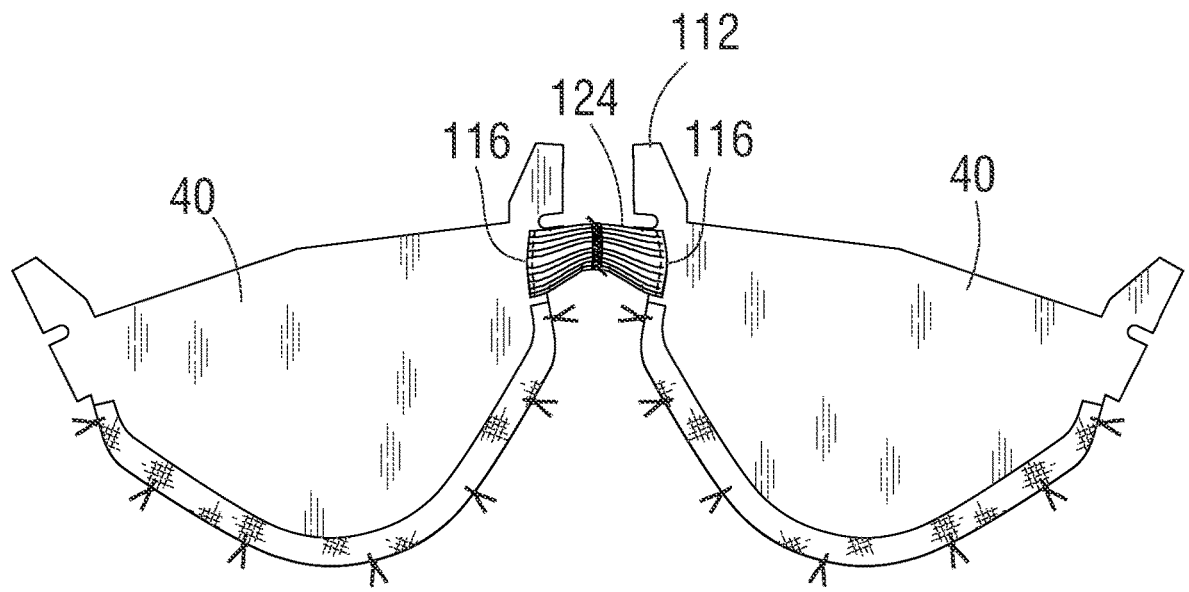
FIGS. 16-17 show the assembly of an exemplary leaflet structure.
Figure 17:
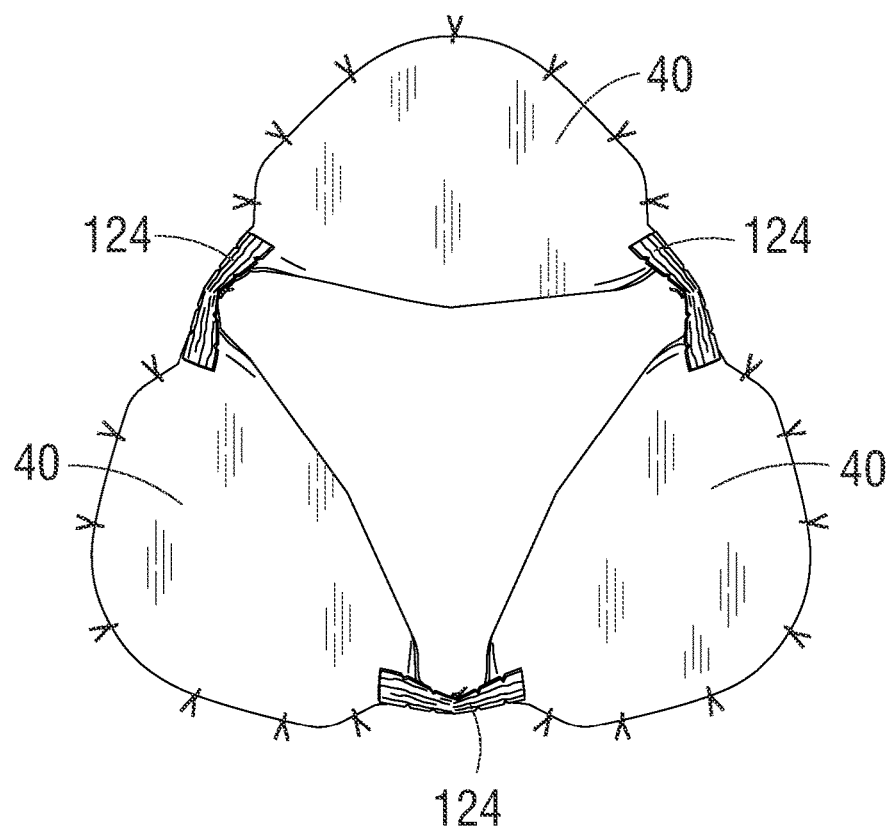

The leaflets 40 can be secured to one another at their adjacent sides to form commissures 122 of the leaflet structure (FIG. 20). A plurality of flexible connectors 124 (one of which is shown in FIG. 16) can be used to interconnect pairs of adjacent sides of the leaflets and to mount the leaflets to the commissure window frame portions 30 (FIG. 5). FIG. 16 shows the adjacent sides of two leaflets 40 interconnected by a flexible connector 124. Three leaflets 40 can be secured to each other side-to-side using three flexible connectors 124, as shown in FIG. 17. Additional information regarding connecting the leaflets to each other, as well as connecting the leaflets to the frame, can be found, for example, in U.S. Patent Application Publication No. 2012/0123529, which is incorporated by reference herein in its entirety.

As noted above, the inner skirt 16 can be used to assist in suturing the leaflet structure 14 to the frame. The inner skirt 16 can have an undulating temporary marking suture to guide the attachment of the lower edges of each leaflet 40. The inner skirt 16 itself can be sutured to the struts of the frame 12 using sutures 70, as noted above, before securing the leaflet structure 14 to the skirt 16. The struts that intersect the marking suture desirably are not attached to the inner skirt 16. This allows the inner skirt 16 to be more pliable in the areas not secured to the frame and minimizes stress concentrations along the suture line that secures the lower edges of the leaflets to the skirt. As noted above, when the skirt is secured to the frame, the fibers 78, 80 of the skirt (see FIG. 12) generally align with the angled struts of the frame to promote uniform crimping and expansion of the frame.

Figure 18:
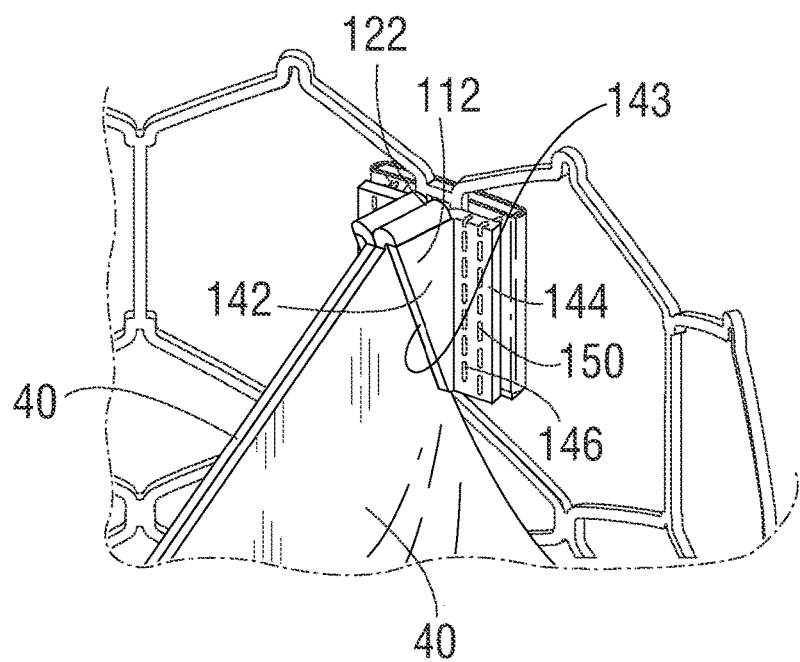
FIG. 18 shows the assembly of commissure portions of the leaflet structure with window frame portions of the frame.

FIG. 18 shows one specific approach for securing the commissure portions 122 of the leaflet structure 14 to the commissure window frame portions 30 of the frame. The flexible connector 124 (FIG. 17) securing two adjacent sides of two leaflets is folded widthwise and the upper tab portions 112 are folded downwardly against the flexible connector. Each upper tab portion 112 is creased lengthwise (vertically) to assume an L-shape having a first portion 142 folded against a surface of the leaflet and a second portion 144 folded against the connector 124. The second portion 144 can then be sutured to the connector 124 along a suture line 146. Next, the commissure tab assembly is inserted through the commissure window 20 of a corresponding window frame portion 30, and the folds outside of the window frame portion 30 can be sutured to portions 144.

FIG. 18 also shows that the folded down upper tab portions 112 can form a double layer of leaflet material at the commissures. The first portions 142 of the upper tab portions 112 are positioned flat against layers of the two leaflets 40 forming the commissures, such that each commissure comprises four layers of leaflet material just inside of the window frames 30. This four-layered portion of the commissures can be more resistant to bending, or articulating, than the portion of the leaflets 40 just radially inward from the relatively more-rigid four-layered portion. This causes the leaflets 40 to articulate primarily at inner edges 143 of the folded-down first portions 142 in response to blood flowing through the prosthetic valve during operation within the body, as opposed to articulating about or proximal to the axial struts of the window frames 30. Because the leaflets articulate at a location spaced radially inwardly from the window frames 30, the leaflets can avoid contact with and damage from the frame. However, under high forces, the four layered portion of the commissures can splay apart about a longitudinal axis adjacent to the window frame 30, with each first portion 142 folding out against the respective second portion 144. For example, this can occur when the prosthetic valve 10 is compressed and mounted onto a delivery shaft, allowing for a smaller crimped diameter. The four-layered portion of the commissures can also splay apart about the longitudinal axis when the balloon catheter is inflated during expansion of the prosthetic valve, which can relieve some of the pressure on the commissures caused by the balloon, reducing potential damage to the commissures during expansion.

After all three commissure tab assemblies are secured to respective window frame portions 30, the lower edges of the leaflets 40 between the commissure tab assemblies can be sutured to the inner skirt 16. For example, as shown in FIG. 19, each leaflet 40 can be sutured to the inner skirt 16 along suture line 154 using, for example, Ethibond Excel® PET thread. The sutures can be in-and-out sutures extending through each leaflet 40, the inner skirt 16, and each reinforcing strip 72. Each leaflet 40 and respective reinforcing strip 72 can be sewn separately to the inner skirt 16. In this manner, the lower edges of the leaflets are secured to the frame 12 via the inner skirt 16. As shown in FIG. 19, the leaflets can be further secured to the skirt with blanket sutures 156 that extend through each reinforcing strip 72, leaflet 40 and the inner skirt 16 while looping around the edges of the reinforcing strips 72 and leaflets 40. The blanket sutures 156 can be formed from PTFE suture material. FIG. 20 shows a side view of the frame 12, leaflet structure 14 and the inner skirt 16 after securing the leaflet structure 14 and the inner skirt 16 to the frame 12 and the leaflet structure 14 to the inner skirt 16.

Figure 21:
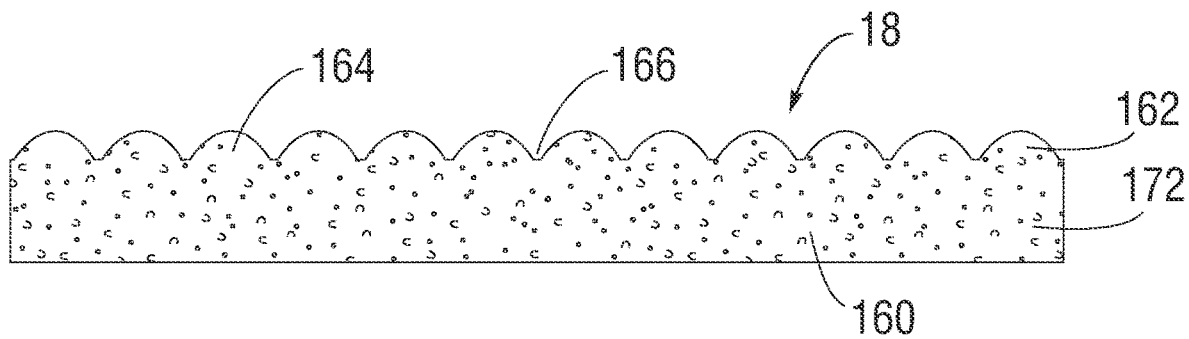
FIGS. 21-23 are different views of an exemplary outer skirt of the prosthetic heart valve of FIG. 1.
Figure 22:
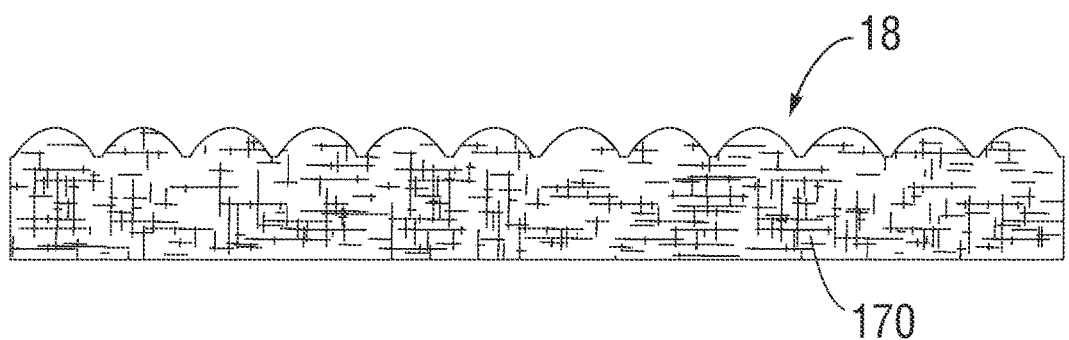
Figure 23:
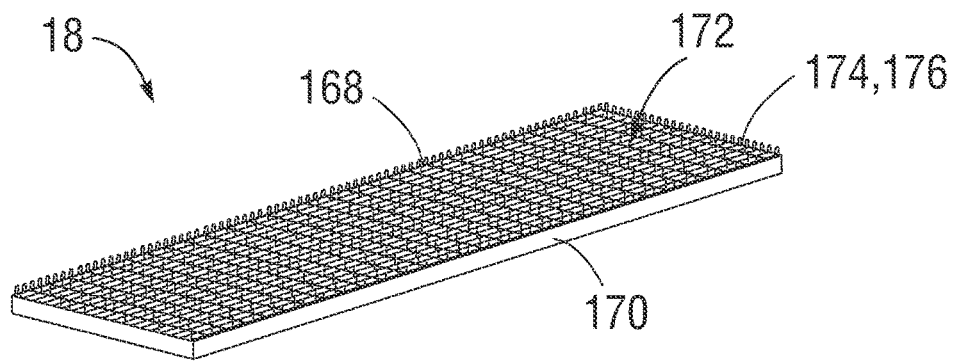

FIG. 21 is a flattened view of the outer skirt 18 prior to its attachment to the frame 12, showing the outer surface of the skirt. FIG. 22 is a flattened view of the outer skirt 18 prior to its attachment to the frame 12, showing the inner surface of the skirt. FIG. 23 is a perspective view of the outer skirt prior to its attachment to the frame 12. The outer skirt 18 can be laser cut or otherwise formed from a strong, durable material such as PET or various other suitable synthetic or natural materials configured to restrict and/or prevent blood-flow therethrough. The outer skirt 18 can comprise a substantially straight lower (inflow or upstream) edge portion 160 and an upper (outflow or downstream) edge portion 162 defining a plurality of alternating projections 164 (which can be tapered as shown) and notches 166, or castellations, that generally follow the shape of a row of struts of the frame. The lower and upper edge portions 160, 162 can have other shapes in alternative embodiments. For example, in one implementation, the lower edge portion 160 can be formed with a plurality of projections generally conforming to the shape of a row of struts of the frame 12, while the upper edge portion 162 can be straight.

In particular embodiments, the outer skirt 18 can comprise at least one soft, plush surface 168 oriented radially outward so as to cushion and seal against native tissues surrounding the prosthetic valve. In certain examples, the outer skirt 18 can be made from any of a variety of woven, knitted, or crocheted fabrics wherein the surface 168 is the surface of a plush nap or pile of the fabric. Exemplary fabrics having a pile include velour, velvet, velveteen, corduroy, terrycloth, fleece, etc. As best shown in FIG. 23, the outer skirt can have a base layer 170 (a first layer) from which a pile layer 172 (a second layer) extends. The base layer 170 can comprise warp and weft yarns woven or knitted into a mesh-like structure. For example, in a representative configuration, the yarns of the base layer 170 can be flat yarns and can have a denier range of from about 7 dtex to about 100 dtex, and can be knitted with a density of from about 20 to about 100 wales per inch and from about 30 to about 110 courses per inch. The yarns can be made from, for example, biocompatible thermoplastic polymers such as PET, PTFE (polytetrafluoroethylene), Nylon, etc., or any other suitable natural or synthetic fibers.

The pile layer 172 can comprise pile yarns 174 woven or knitted into loops. In certain configurations, the pile yarns 174 can be the warp yarns or the weft yarns of the base layer 170 woven or knitted to form the loops. The pile yarns 174 can also be separate yarns incorporated into the base layer, depending upon the particular characteristics desired. In a representative configuration, the pile yarns 174 can be flat yarns and can have a denier range of from about 7 dtex to about 100 dtex, and can be knitted with a density of from about 20 to about 100 wales per inch and from about 30 to about 110 courses per inch. The pile yarns can be made from, for example, biocompatible thermoplastic polymers such as PET, PTFE, Nylon, etc., or any other suitable natural or synthetic fibers.

In certain embodiments, the loops can be cut such that the pile layer 172 is a cut pile in the manner of, for example, a velour fabric. FIGS. 1 and 21 illustrate a representative embodiment of the outer skirt 18 configured as a velour fabric. In other embodiments, the loops can be left intact to form a looped pile in the manner of, for example, terrycloth. FIG. 23 illustrates a representative embodiment of the outer skirt 18 in which the pile yarns 174 are knitted to form loops 176.

The height of the pile yarns 174 (e.g., the loops 176) can be the same for all pile yarns across the entire extent of the outer skirt so as to provide an outer skirt having a constant thickness. In alternative embodiments, the height of the pile yarns 174 can vary along the height and/or circumference of the outer skirt so as to vary the thickness of the outer skirt along its height and/or circumference, as further described below.

The pile layer 172 has a much greater surface area than similarly sized skirts formed from flat or woven materials, and therefore can enhance tissue ingrowth compared to known skirts. Promoting tissue growth into the pile layer 172 can decrease perivalvular leakage, increase retention of the valve at the implant site and contribute to long-term stability of the valve. In some configurations, the surface area of the pile yarns 174 can be further increased by using textured yarns having an increased surface area due to, for example, a wavy or undulating structure. In configurations such as the looped pile embodiment of FIG. 23, the loop structure and the increased surface area provided by the textured yarn of the loops 176 can allow the loops to act as a scaffold for tissue growth into and around the loops of the pile.

The outer skirt embodiments described herein can also contribute to improved compressibility and shape memory properties of the outer skirt over known valve coverings and skirts. For example, the pile layer 172 can be compliant such that it compresses under load (e.g., when in contact with tissue, other implants, or the like), and returns to its original size and shape when the load is relieved. This can help to improve sealing between the outer skirt and the tissue of the native annulus, or a surrounding support structure in which the prosthetic valve is deployed. Embodiments of an implantable support structure that is adapted to receive a prosthetic valve and retain it within the native mitral valve are disclosed in Application No. 62/449,320, filed Jan. 23, 2017, and application Ser. No. 15/876,053, filed Jan. 19, 2018, which are incorporated herein by reference. The compressibility provided by the pile layer 172 of the outer skirt 18 is also beneficial in reducing the crimp profile of the valve. Additionally, the outer skirt 18 can prevent the leaflets 40 or portions thereof from extending through spaces between the struts of the frame 12 as the prosthetic valve is crimped, thereby protecting against damage to the leaflets due to pinching of the leaflets between struts.

In alternative embodiments, the outer skirt 18 be made of a non-woven fabric such as felt, or fibers such as non-woven cotton fibers. The outer skirt 18 can also be made of porous or spongey materials such as, for example, any of a variety of compliant polymeric foam materials, or woven fabrics, such as woven PET.

Figure 2:
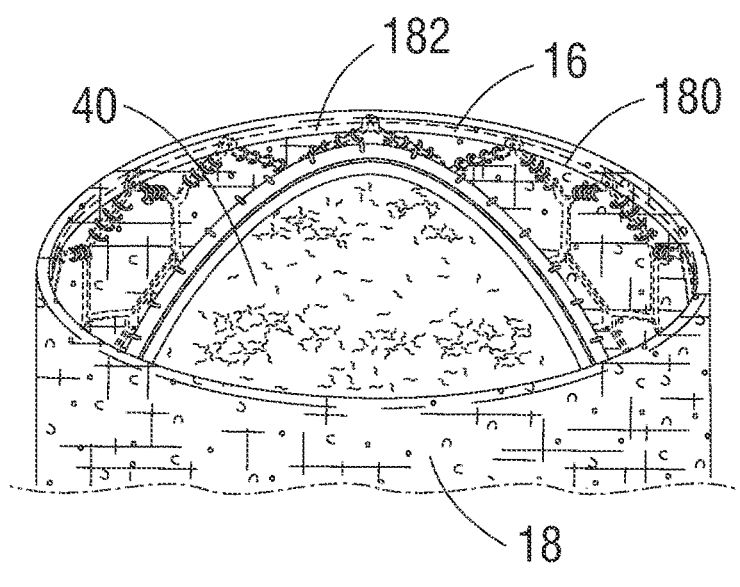
FIG. 2 is an enlarged, perspective view of the inflow end portion of the prosthetic heart valve of FIG. 1.
Figure 3:
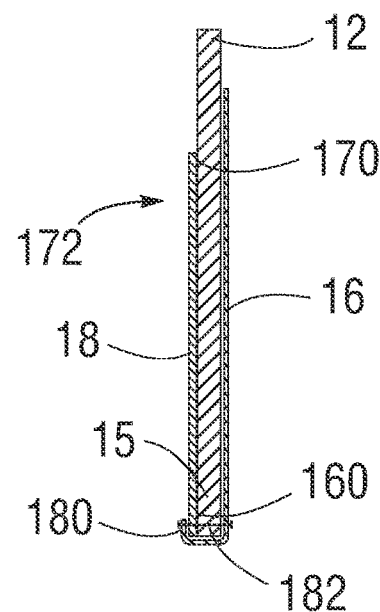
FIG. 3 is a cross-sectional view of the prosthetic heart valve of FIG. 1, showing the attachment of the outer skirt to the inner skirt and the frame.
Figure 9:
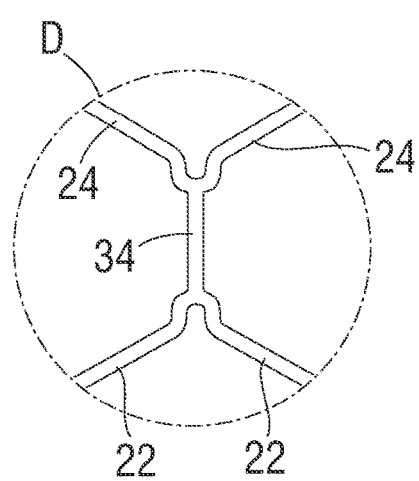
Figure 10:
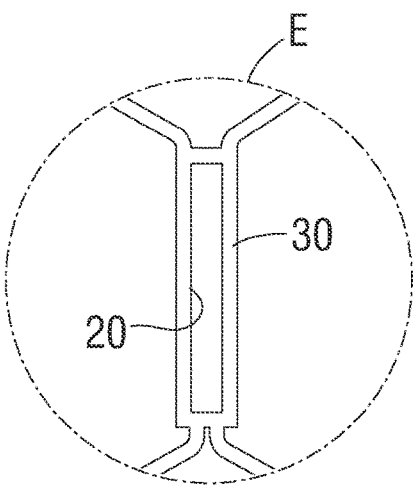
Figure 11:
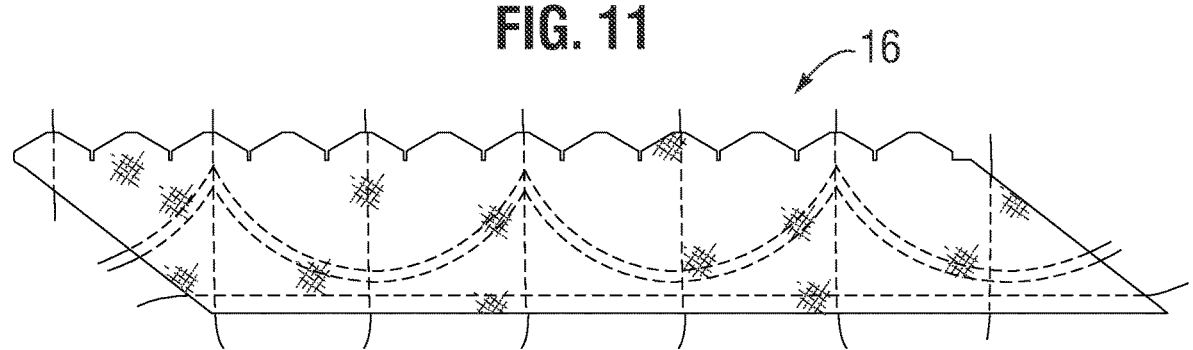
FIGS. 11-12 show an exemplary inner skirt of the prosthetic heart valve of FIG. 1.

Various techniques and configurations can be used to secure the outer skirt 18 to the frame 12 and/or the inner skirt 16. As best shown in FIG. 3, a lower edge portion 180 of the inner skirt 16 can be wrapped around the inflow end 15 of the frame 12, and the lower edge portion 160 of the outer skirt 18 can be attached to the lower edge portion 180 of the inner skirt 16 and/or the frame 12, such as with one or more sutures or stitches 182 (as best shown in FIG. 2) and/or an adhesive. In lieu of or in addition to sutures, the outer skirt 18 can be attached to the inner skirt 16, for example, by ultrasonic welding. In the illustrated embodiment, the lower edge portion 160 of the outer skirt 18 can be free of loops, and the lower edge portion 180 of the inner skirt 16 can overlap and can be secured to the base layer 170 of the outer skirt 18. In other embodiments, the lower edge portion 180 of the inner skirt 16 can extend over one or more rows of loops 176 of the pile layer 172 (see FIG. 27), as further described below. In other embodiments, the lower edge portion 180 of the inner skirt 18 can be wrapped around the inflow end of the frame and extend between the outer surface of the frame and the outer skirt 18 (i.e., the outer skirt 18 is radially outward of the lower edge portion 180 of the inner skirt 18).

As shown in FIG. 1, each projection 164 of the outer skirt 18 can be attached to the third row III of struts 26 (FIG. 5) of the frame 12. The projections 164 can, for example, be wrapped over respective struts 26 of row III and secured with sutures 184. The outer skirt 18 can be further secured to the frame 12 by suturing an intermediate portion of the outer skirt (a portion between the lower and upper edge portions) to struts of the frame, such as struts 24 of the second row II of struts. As shown in FIG. 1, the projections 164 can be shaped to correspond to the zig-zig pattern of the third row III of struts 26. As further shown in FIG. 1, each projection 164 can comprise two angled side edges that converge at a peak of the projection and each side edge converges with an adjacent side edge of an adjacent projection at a valley between adjacent projections, wherein each peak is positioned at a first junction of the third row of struts and each valley is positioned at a second junction of the third row of struts.

The height of the outer skirt (as measured from the lower edge to the upper edge) can vary in alternative embodiments. For example, in some embodiments, the outer skirt can cover the entire outer surface of the frame 12, with the lower edge portion 160 secured to the inflow end of the frame 12 and the upper edge portion secured to the outflow end of the frame. In another embodiment, the outer skirt 18 can extend from the inflow end of the frame to the second row II of struts 24, or to the fourth row IV of struts 28, or to a location along the frame between two rows of struts. In still other embodiments, the outer skirt 18 need not extend all the way to the inflow end of the frame, and instead the inflow end of the outer skirt can secured to another location on the frame, such as to the second row II of struts 24.

The outer skirt 18 desirably is sized and shaped relative to the frame such that when the prosthetic valve 10 is in its radially expanded state, the outer skirt 18 fits snugly (in a tight-fitting manner) against the outer surface of the frame. When the prosthetic valve 10 is radially compressed to a compressed state for delivery, the portion of the frame on which the outer skirt is mounted can elongate axially. The outer skirt 18 desirably has sufficient elasticity to stretch in the axial direction upon radial compression of the frame so that it does not to prevent full radial compression of the frame or deform the struts during the crimping process.

Known skirts that have material slack or folds when the prosthetic valve is expanded to its functional size are difficult to assemble because the material must be adjusted as it is sutured to the frame. In contrast, because the outer skirt 18 is sized to fit snugly around the frame in its fully expanded state, the assembly process of securing the skirt to the frame is greatly simplified. During the assembly process, the outer skirt can be placed around the frame with the frame in its fully expanded state and the outer skirt in its final shape and position when the valve is fully functional. In this position, the skirt can then be sutured to the frame and/or the inner skirt. This simplifies the suturing process compared to skirts that are designed to have slack or folds when radially expanded.

Figure 24:
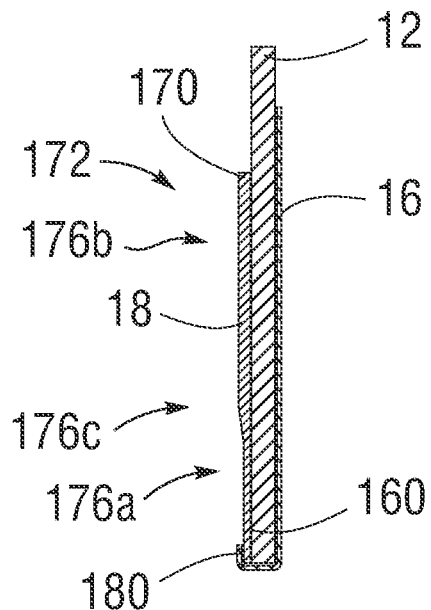
FIG. 24-26 are cross-sectional views similar to FIG. 3 but showing different embodiments of the outer skirt.

As shown in FIG. 3, the height of the loops of the pile layer 172 can be constant across the entire extent of the outer skirt such that the outer skirt 18 has a constant thickness, except along the upper and lower edge portions which can be free of loops to facilitate attachment of the outer skirt to the frame and/or the inner skirt 16. The "height" of the loops is measured in the radial direction when the skirt is mounted on the frame. In another embodiment, as shown in FIG. 24, the loops can comprise lower loops 176a along the lower or upstream portion of the skirt that are relatively shorter in height (as represented by a thinner cross-sectional area) than upper loops 176b (as represented by a thicker cross-sectional area) along the upper or downstream portion of the skirt. The skirt 18 can further include a group of intermediate loops 176c that gradually increase in height from the lower loops 176a to the upper loops 176b. Thus, in the embodiment of FIG. 24, the thickness of outer skirt 18 increases from a minimum thickness along the lower portion to a maximum thickness along the upper portion.

Figure 25:
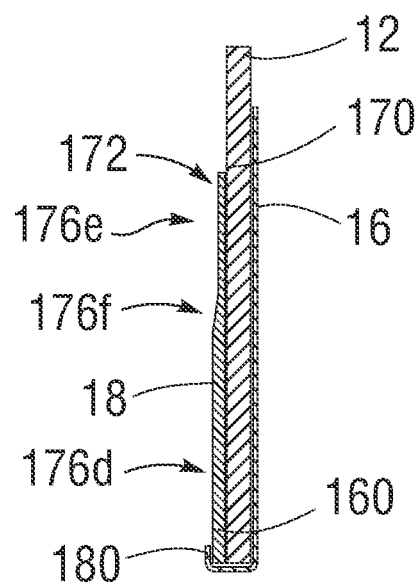

FIG. 25 shows another embodiment in which the loops of the outer skirt comprise lower loops 176d along the lower portion of the skirt that are relatively higher or longer in height than upper loops 176e along the upper portion of the skirt. The skirt 18 can further include a group of intermediate loops 176f that gradually decrease in height from the lower loops 176d to the upper loops 176e. Thus, in the embodiment of FIG. 25, the thickness of outer skirt 18 decreases from a maximum thickness along the lower portion to a minimum thickness along the upper portion.

Figure 26:
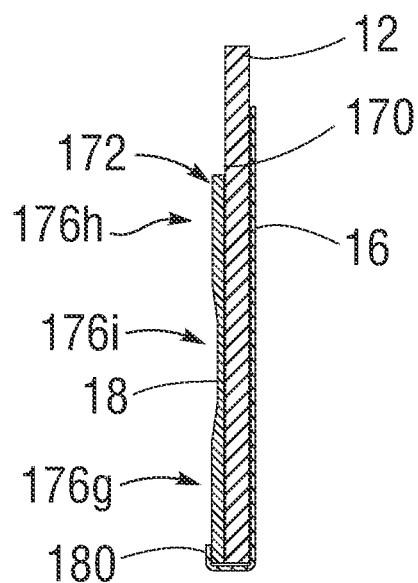

FIG. 26 shows another embodiment in which the loops comprise lower loops 176g, upper loops 176h, and intermediate loops 176i that are relative shorter in height than the lower and upper loops. As shown, the lower loops 176g can gradually decrease in height from the lower edge of the skirt toward the intermediate loops 176i, and the upper loops 176h can gradually decrease in height from the upper edge of the skirt toward the intermediate loops 176i. Thus, in the embodiment of FIG. 26, the thickness of the outer skirt decreases from a maximum thickness along the lower portion to a minimum thickness along the intermediate portion, and then increases from the intermediate portion to the maximum thickness along the upper portion. In the illustrated embodiment, the upper portion of the skirt containing the upper loops 176h has the same thickness as the lower portion of the skirt containing the lower loops 176g. In other embodiments, the thickness of the upper portion of the skirt containing the upper loops 176h can be greater or less than the same thickness of the lower portion of the skirt containing the lower loops 176g.

Further, in any of the embodiments described above where the height of the loops vary along the height of the skirt, the height of the loops need not vary gradually from one section of the skirt to another section of the skirt. Thus, an outer skirt can have loops of different heights, wherein the height of the loops change abruptly at locations along the skirt. For example, in the embodiment of FIG. 24, the lower portion of the skirt containing the lower loops 176a can extend all the way to the upper portion of the skirt containing the upper loops 176g without the intermediate loops 176c forming a transition between the upper and lower portions.

In lieu of or in addition to having loops that vary in height along the height of the skirt, the height of the loops 176 (and therefore the thickness of the outer skirt) can vary along the circumference of the outer skirt. For example, the height of the loops can be increased along circumferential sections of the skirt where larger gaps might be expected between the outer skirt and the native annulus, such as circumferential sections of the skirt that are aligned with the commissures of the native valve.

Figure 27:
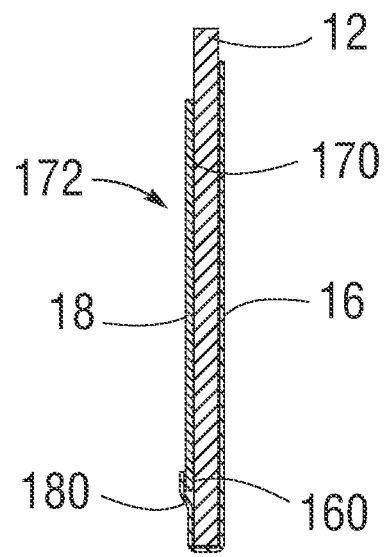
FIGS. 27-28 show an alternative way of securing an outer skirt to an inner skirt and/or the frame of a prosthetic heart valve.
Figure 28:
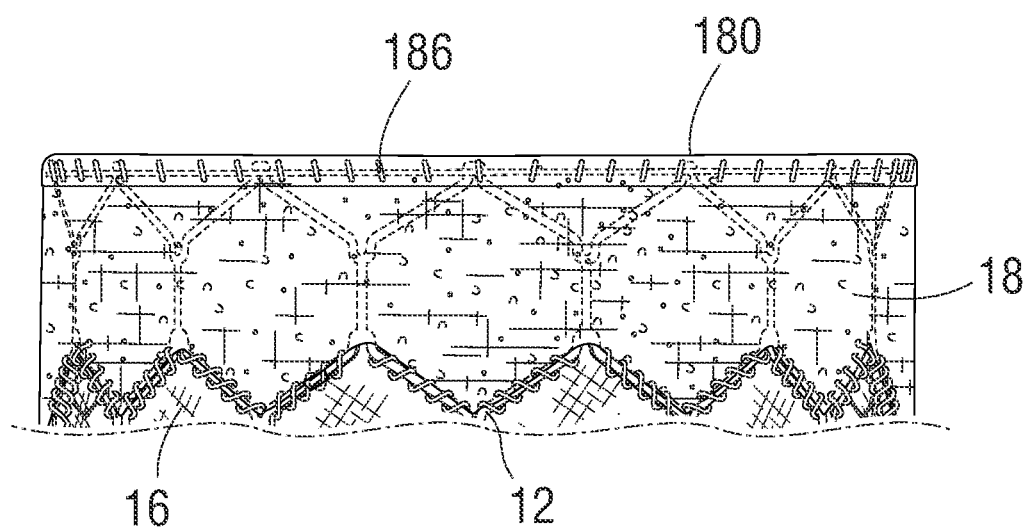

FIGS. 27 and 28 show an alternative configuration for mounting the outer skirt 18 to the frame 12. In this embodiment, as best shown in FIG. 27, the lower edge portion 180 of the inner skirt 16 is wrapped around the inflow end of the frame and extended over one or more rows of loops along the lower edge portion 160 of the outer skirt. The lower edge portion 180 of the inner skirt 16 can then be secured to the lower edge portion 160 of the outer skirt, such as with sutures or stitching 186 (FIG. 28), an adhesive, and/or welding (e.g., ultrasonic welding). The stitching 186 can also extend around selected struts adjacent the inflow end of the frame. The lower edge portion 180 of the inner skirt is effective to partially compress the loops of the pile layer 172, which creates a tapered edge at the inflow end of the prosthetic valve. The tapered edge reduces the insertion force required to push the prosthetic valve through an introducer sheath when being inserted into a patient's body. In one specific implementation, the stitching 186 secures the lower edge portion 180 of the inner skirt to the outer skirt 18 at a distance of at least 1 mm from the lowermost edge of the outer skirt. The upper edge portion 162 and the intermediate portion of the outer skirt can then be secured to the frame as previously described.

Figure 29:
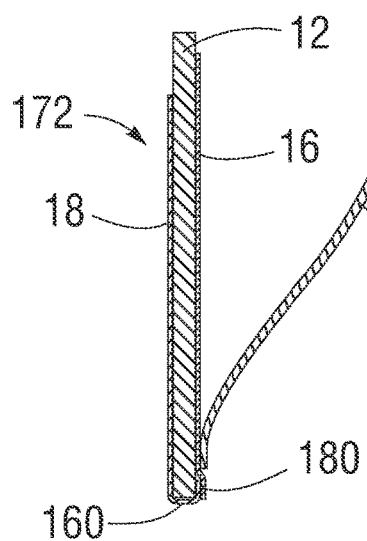
FIGS. 29-32 show another way of securing an outer skirt to an inner skirt and/or the frame of a prosthetic heart valve.
Figure 30:
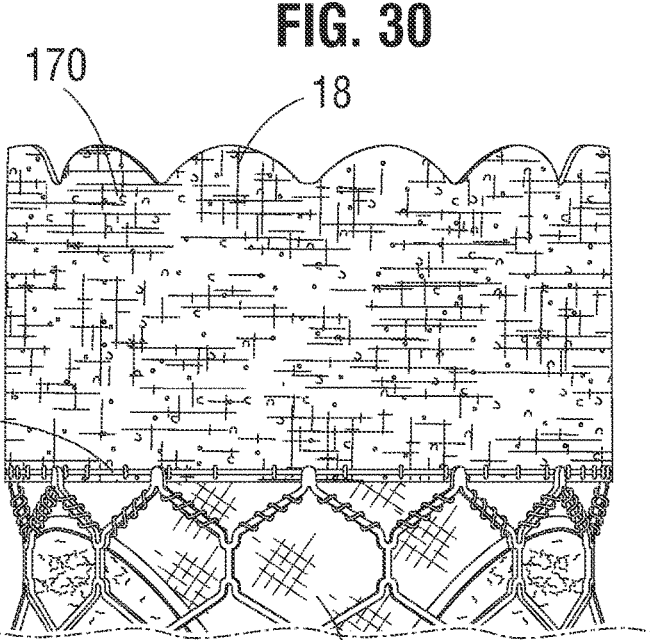
Figure 31:
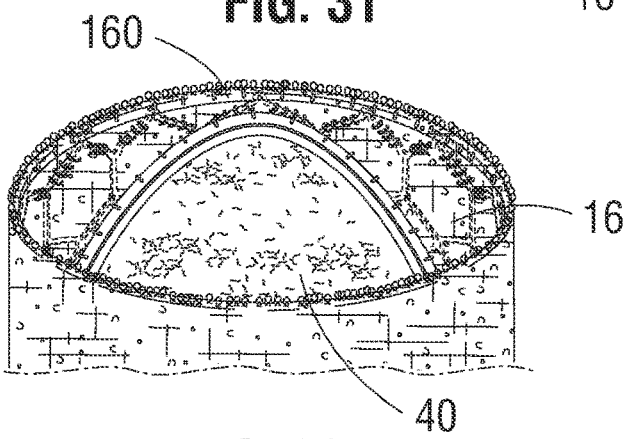
Figure 32:
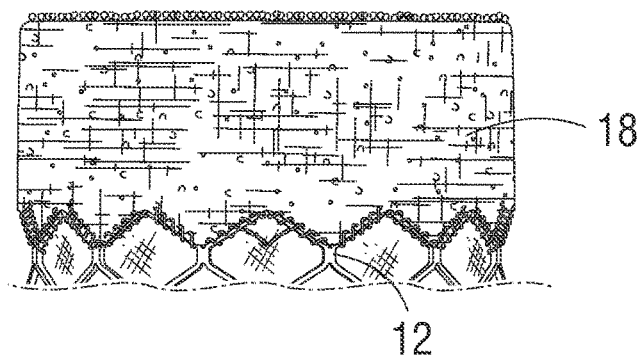

FIGS. 29-32 show another configuration for mounting the outer skirt 18 to the frame 12. In this embodiment, the outer skirt 18 is initially placed in a tubular configuration with the base layer 170 facing outwardly and the lower edge portion 160 (which can be free of loops 176) can be placed between the inner surface of the frame 12 and the lower edge portion 180 of the inner skirt 16, as depicted in FIG. 30. The lower edge portions of the outer skirt and the inner skirt can be secured to each other, such as with stitches, an adhesive, and/or welding (e.g., ultrasonic welding). In one implementation, the lower edge portions of the outer skirt and the inner skirt are secured to each other with in-and-out stitches and locking stitches. The outer skirt 18 is then inverted and pulled upwardly around the outer surface of the frame 12 such that the base layer 170 is placed against the outer surface of the frame and the pile layer 172 faces outwardly, as depicted in FIG. 29. In this assembled configuration, the lower edge portion 160 of the outer skirt wraps around the inflow end of the frame and is secured to the inner skirt inside of the frame. The upper edge portion 162 and the intermediate portion of the outer skirt can then be secured to the frame as previously described.

The prosthetic valve 10 can be configured for and mounted on a suitable delivery apparatus for implantation in a subject. Several catheter-based delivery apparatuses are known; a non-limiting example of a suitable catheter-based delivery apparatus includes that disclosed in U.S. Patent Application Publication No. 2013/0030519, which is incorporated by reference herein in its entirety, and U.S. Patent Application Publication No. 2012/0123529.

To implant a plastically-expandable prosthetic valve 10 within a patient, the prosthetic valve 10 including the outer skirt 18 can be crimped on an elongated shaft of a delivery apparatus. The prosthetic valve, together with the delivery apparatus, can form a delivery assembly for implanting the prosthetic valve 10 in a patient's body. The shaft can comprise an inflatable balloon for expanding the prosthetic valve within the body. With the balloon deflated, the prosthetic valve 10 can then be percutaneously delivered to a desired implantation location (e.g., a native aortic valve region). Once the prosthetic valve 10 is delivered to the implantation site (e.g., the native aortic valve) inside the body, the prosthetic valve 10 can be radially expanded to its functional state by inflating the balloon or equivalent expansion mechanism.

The outer skirt 18 can fill-in gaps between the frame 12 and the surrounding native annulus to assist in forming a good, fluid-tight seal between the prosthetic valve 10 and the native annulus. The outer skirt 18 therefore cooperates with the inner skirt 16 to avoid perivalvular leakage after implantation of the prosthetic valve 10. Additionally, as discussed above, the pile layer of the outer skirt further enhances perivalvular sealing by promoting tissue ingrowth with the surrounding tissue.

Alternatively, a self-expanding prosthetic valve 10 can be crimped to a radially collapsed configuration and restrained in the collapsed configuration by inserting the prosthetic valve 10, including the outer skirt 18, into a sheath or equivalent mechanism of a delivery catheter. The prosthetic valve 10 can then be percutaneously delivered to a desired implantation location. Once inside the body, the prosthetic valve 10 can be advanced from the delivery sheath, which allows the prosthetic valve to expand to its functional state.

Figure 33:
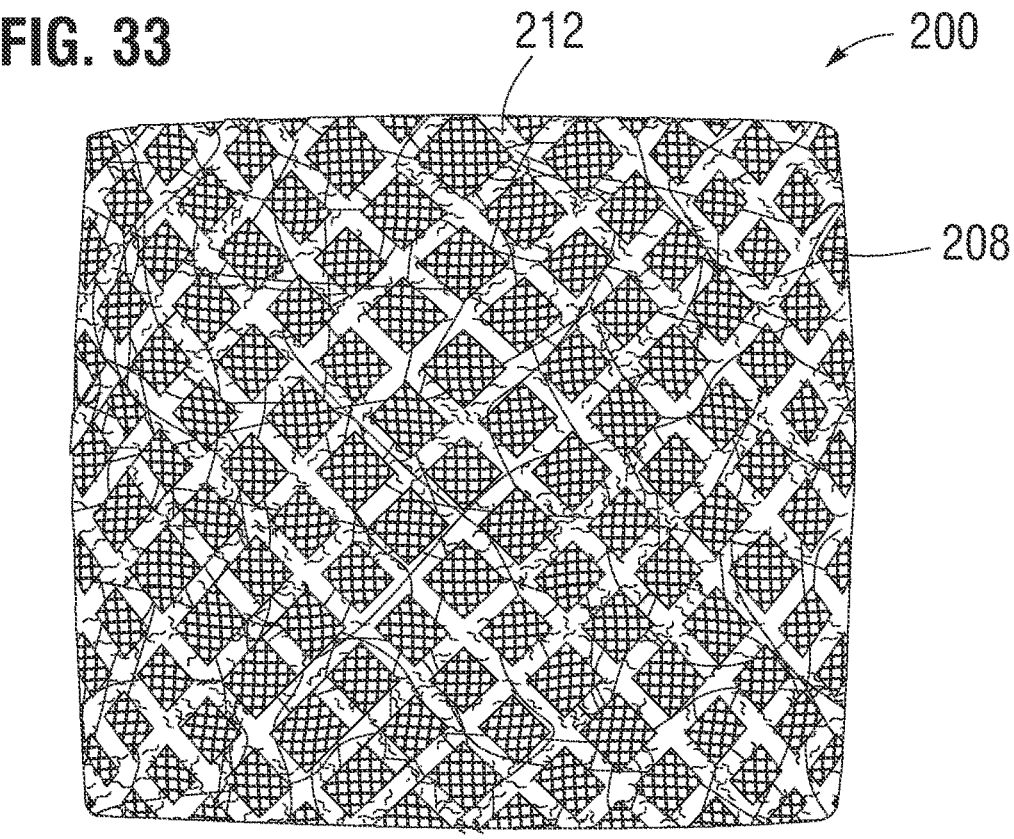
FIGS. 33-35 show another embodiment of an outer sealing member for a prosthetic heart valve.

FIG. 33 illustrates a sealing member 200 for a prosthetic valve, according to another embodiment. The sealing member 200 in the illustrated embodiment is formed from a spacer fabric. The sealing member 200 can be positioned around the outer surface of the frame 12 of a prosthetic valve (in place of the outer skirt 18) and secured to the inner skirt 16 and/or the frame using stitching, an adhesive, and/or welding (e.g., ultrasonic welding).

Figure 34:
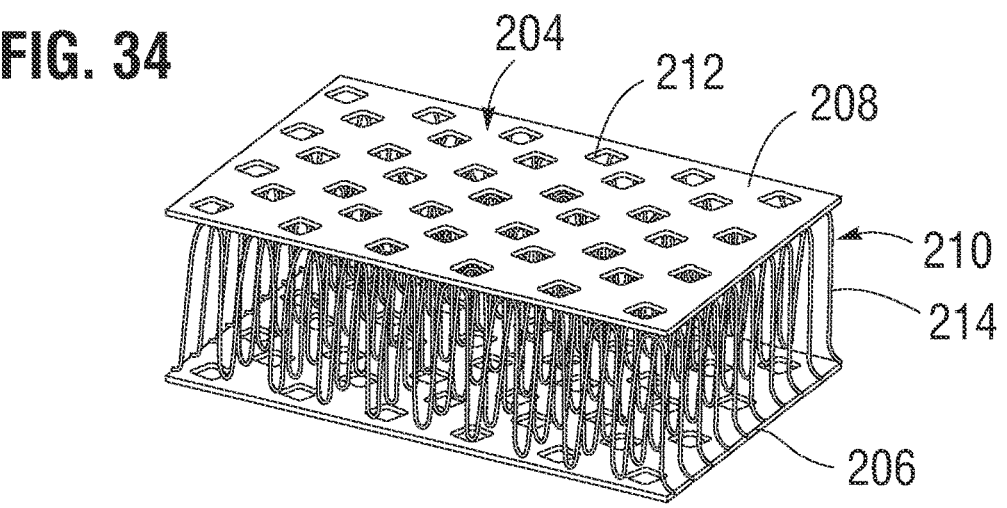

As best shown in FIG. 34, the spacer fabric can comprise a first, inner layer 206, a second, outer layer 208, and an intermediate spacer layer 210 extending between the first and second layers to create a three-dimensional fabric. The first and second layers 206, 208 can be woven fabric or mesh layers. In certain configurations, one or more of the first and second layers 206, 208 can be woven such that they define a plurality of openings 212. In some examples, openings such as the openings 212 can promote tissue growth into the sealing member 200. In other embodiments, the layers 206, 208 need not define openings, but can be porous, as desired.

Figure 35:
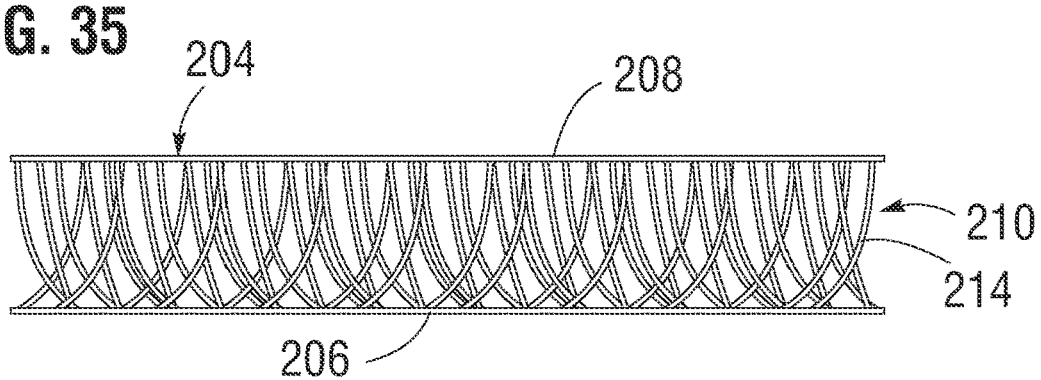

The spacer layer 210 can comprise a plurality of pile yarns 214. The pile yarns 214 can be, for example, monofilament yarns arranged to form a scaffold-like structure between the first and second layers 206, 208. For example, FIGS. 34 and 35 illustrate an embodiment in which the pile yarns 214 extend between the first and second layers 206, 208 in a sinusoidal or looping pattern.

In certain examples, the pile yarns 214 can have a rigidity that is greater than the rigidity of the fabric of the first and second layers 206, 208 such that the pile yarns 214 can extend between the first and second layers 206, 208 without collapsing under the weight of the second layer 208. The pile yarns 214 can also be sufficiently resilient such that the pile yarns can bend or give when subjected to a load, allowing the fabric to compress, and return to their non-deflected state when the load is removed. For example, when the prosthetic valve is radially compressed for delivery into a patient's body and placed in a delivery sheath of a delivery apparatus or advanced through an introducer sheath, the pile yarns 214 can compress to reduce the overall crimp profile of the prosthetic valve, and then return to their non-deflected state when deployed from the delivery sheath or the introducer sheath, as the case may be.

The spacer fabric can be warp-knitted, or weft-knitted, as desired. Some configurations of the spacer cloth can be made on a double-bar knitting machine. In a representative example, the yarns of the first and second layers 206, 208 can have a denier range of from about 10 dtex to about 70 dtex, and the yarns of the monofilament pile yarns 214 can have a denier range of from about 2 mil to about 10 mil. The pile yarns 214 can have a knitting density of from about 20 to about 100 wales per inch, and from about 30 to about 110 courses per inch. Additionally, in some configurations (e.g., warp-knitted spacer fabrics) materials with different flexibility properties may be incorporated into the spacer cloth to improve the overall flexibility of the spacer cloth.

Figure 36:
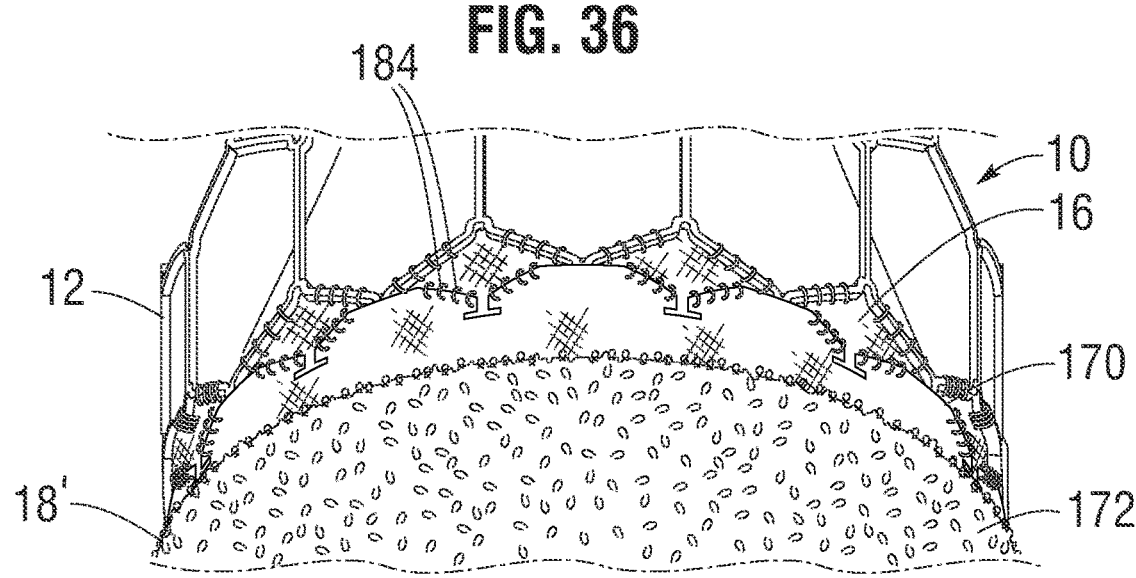
FIG. 36 shows another embodiment of an outer sealing member, shown mounted on the frame of a prosthetic heart valve.
Figure 37:
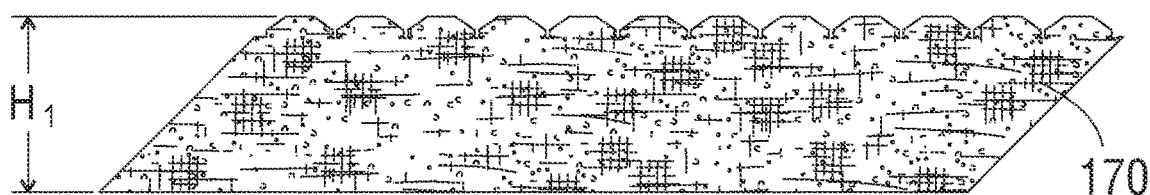
FIG. 37 is a flattened view of a woven mesh layer of the sealing member of FIG. 36.
Figure 38:
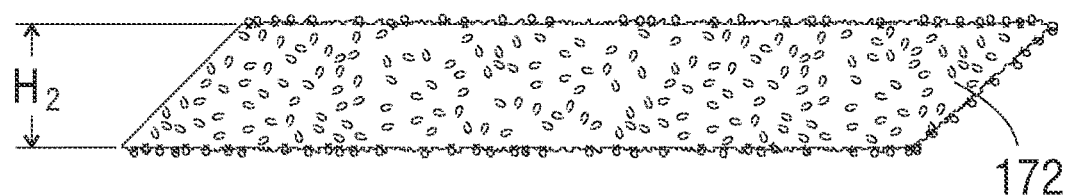
FIG. 38 is a flattened view of a pile layer of the sealing member of FIG. 36.

FIG. 36 shows an outer sealing member 18' mounted on the outside of the frame 12 of a prosthetic heart valve 10, according to another embodiment. FIG. 37 shows the base layer 170 of the sealing member 18' in a flattened configuration. FIG. 38 shows the pile layer 172 of the sealing member 18' in a flattened configuration. The outer sealing member 18' is similar to the sealing member 18 of FIGS. 1 and 21-23, except that the height ($H_1$) of the base layer 170 is greater than the height (H 2) of the pile layer 172. Like the previously described embodiments, the sealing member 18' desirably is sized and shaped relative to the frame 12 such that when the prosthetic valve is in its radially expanded state, both layers 170, 172 of the sealing member 18 fit snugly (in a tight-fitting manner) around the outer surface of the frame.

In the illustrated configuration, the base layer 170 extends axially from the inlet end of the frame 12 to the third row III of struts 26 of the frame 12. The upstream and downstream edges of the base layer 170 can be sutured to the struts 22 of the first row I and to the struts 26 of the third row III with sutures 182 and 184, respectively, as previously described. The pile layer 172 in the illustrated configuration extends from the inlet end of the frame 12 to a plane that intersects the frame at the nodes formed at the intersection of the upper ends of struts 24 of the second row II and the lower ends of struts 26 of the third row III, wherein the plane is perpendicular to the central axis of the frame.

The pile layer 172 can be separately formed from and subsequently attached to the base layer 170, such as with sutures, an adhesive, and/or welding. Alternatively, the pile layer 172 can be formed from yarns or fibers woven into the base layer 170. The pile layer 172 can have any of the configurations shown in FIGS. 24-26.

In particular embodiments, the height H of the base layer 170 can be about 9 mm to about 25 mm or about 13 mm to about 20 mm, with about 19 mm being a specific example. The height $H_2$ of the pile layer 172 can be at least 2 mm less than $H_1$, at least 3 ram less than $H_1$, at least 4 mm less than $H_1$, at least 5 mm less than $H_1$, at least 6 mm less than $H_1$, at least 7 mm less than $H_1$, at least 8 mm less than $H_1$, at least 9 ram than $H_1$, or at least 10 mm less than $H_1$. The height of the frame 12 in the radially expanded state can be about 12 mm to about 27 mm or about 15 mm to about 23 mm, with about 20 mm being a specific example.

The relatively shorter pile layer 172 reduces the crimp profile along the mid-section of the prosthetic valve 10 but still provides for enhanced paravalvular sealing along the majority of the landing zone of the prosthetic valve. The base layer 170 also provides a sealing function downstream of the downstream edge of the pile layer 172.

Figure 39A:
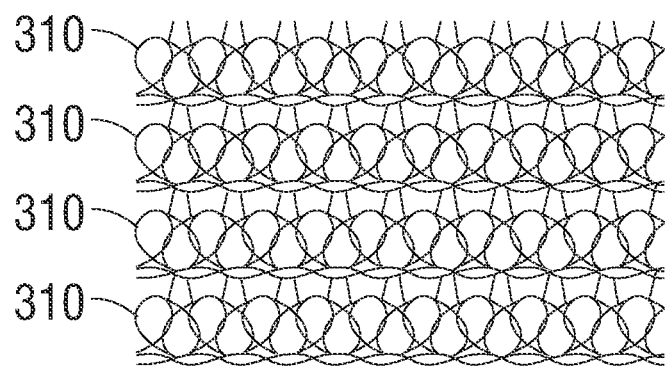
FIG. 39A is a magnified view of a portion of the sealing member of FIG. 39.
Figure 40A:
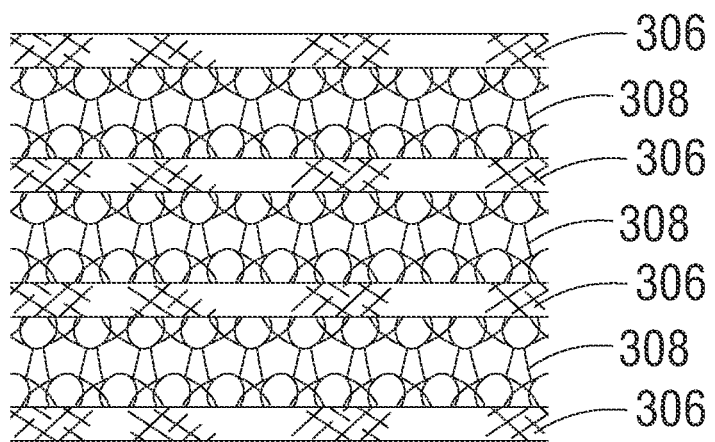
FIG. 40A is a magnified view of a portion of the sealing member of FIG. 40.

FIGS. 39-40 show an outer sealing member 300 for a prosthetic heart valve (e.g., a prosthetic heart valve 10), according to another embodiment. FIGS. 39A and 40A are magnified views of portions of the sealing member shown in FIGS. 39 and 40, respectively. The sealing member 300 can be mounted on the outside of the frame 12 of a prosthetic valve 10 in lieu of sealing member 18 using, for example, sutures, ultrasonic welding, or any other suitable attachment method. Like the previously described embodiments, the sealing member 300 desirably is sized and shaped relative to the frame 12 such that when the prosthetic valve is in its radially expanded state, the sealing member 300 fits snugly (in a tight-fitting manner) against the outer surface of the frame.

The sealing member 300, like sealing members 18, 18', can be a dual-layer fabric comprising a base layer 302 and a pile layer 304. FIG. 39 shows the outer surface of the sealing member 300 defined by the pile layer 304. FIG. 40 shows the inner surface of the sealing member 300 defined by the base layer 302. The base layer 302 in the illustrated configuration comprises a mesh weave having circumferentially extending rows or stripes 306 of higher-density mesh portions interspersed with rows or stripes 308 of lower-density mesh portions.

In particular embodiments, the yarn count of yarns extending in the circumferential direction (side-to-side or horizontally in FIGS. 40 and 40A) is greater in the higher-density rows 306 than in the lower-density rows 308. In other embodiments, the yarn count of yarns extending in the circumferential direction and the yarn count of yarns extending in the axial direction (vertically in FIGS. 40 and 40A) is greater in the higher-density rows 306 than in the lower-density rows 308.

The pile layer 304 can be formed from yarns woven into the base layer 302. For example, the pile layer 304 can comprise a velour weave formed from yarns incorporated in the base layer 302. The pile layer 304 can comprise circumferentially extending rows or stripes 310 of pile formed at axially-spaced locations along the height of the sealing member 300 such that there are axial extending gaps between adjacent rows 310. In this manner, the density of the pile layer varies along the height of the sealing member. In alternative embodiments, the pile layer 304 can be formed without gaps between adjacent rows of pile, but the pile layer can comprise circumferentially extending rows or stripes of higher-density pile interspersed with rows or stripes 312 of lower-density pile.

In alternative embodiments, the base layer 302 can comprise a uniform mesh weave (the density of the weave pattern is uniform) and the pile layer 304 has a varying density.

Varying the density of the pile layer 304 and/or the base layer 302 along the height of the sealing member 300 is advantageous in that it facilitates axially elongation of the sealing member 300 caused by axial elongation of the frame 12 when the prosthetic heart valve is crimped to a radially compressed state for delivery. The varying density also reduces the bulkiness of the sealing member in the radially collapsed state and therefore reduces the overall crimp profile of the prosthetic heart valve.

In alternative embodiments, the density of the sealing member 300 can vary along the circumference of the sealing member to reduce the bulkiness of the sealing member in the radially collapsed state. For example, the pile layer 304 can comprise a plurality of axially-extending, circumferentially-spaced, rows of pile yarns, or alternatively, alternating axially-extending rows of higher-density pile interspersed with axially-extending rows of lower-density pile. Similarly, the base layer 302 can comprise a plurality axially-extending rows of higher-density mesh interspersed with rows of lower-density mesh.

In other embodiments, the sealing member 300 can include a base layer 302 and/or a pile layer 304 that varies in density along the circumference of the sealing member and along the height of the sealing member.

Figure 41:
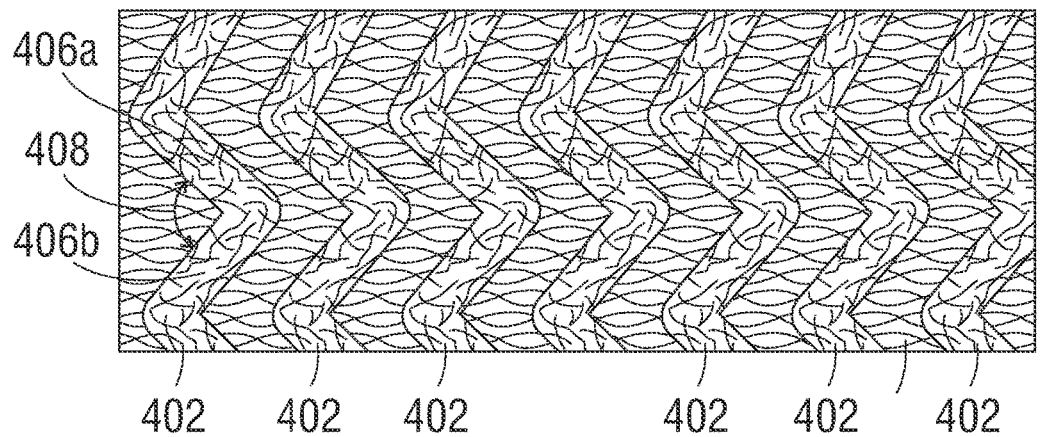
FIG. 41 is flattened view of an outer sealing member for a prosthetic heart valve shown in a relaxed state when the prosthetic heart valve is radially expanded to its functional size, according to another embodiment.

In other embodiments, a sealing member can be knitted, crocheted, or woven to have rows or sections of higher stitch density and rows or sections of lower stitch density without two distinct layers. FIG. 41, for example, shows a sealing member 400 comprising a fabric having a plurality of axially-extending rows 402 of higher-density stitching alternating with axially-extending rows 404 of lower-density stitching. The sealing member 400 can be formed, for example, by knitting, crocheting, or weaving a single layer fabric having rows 402, 404 formed by increasing the stitch density along the rows 402 and decreasing the stitch density along the rows 404 while the fabric is formed. The sealing member 400 can be mounted on the outside of the frame 12 of a prosthetic valve 10 in lieu of sealing member 18 using, for example, sutures, ultrasonic welding, or any other suitable attachment method. Like the previously described embodiments, the sealing member 400 desirably is sized and shaped relative to the frame 12 such that when the prosthetic valve is in its radially expanded state, the sealing member 400 fits snugly (in a tight-fitting manner) against the outer surface of the frame.

The sealing member 400 can be resiliently stretchable between a first, substantially relaxed, axially foreshortened configuration (FIG. 41) corresponding to a radially expanded state of the prosthetic valve, and a second, axially elongated, or tensioned configuration (FIG. 42) corresponding to a radially compressed state of the prosthetic valve. As shown in FIG. 41, when the prosthetic valve is radially expanded and the sealing member 400 is in the first configuration, the higher-density rows 402 extend in an undulating pattern from the lower (upstream edge) to the upper (downstream edge) of the sealing member 400. In the illustrated embodiment, for example, each of the higher-density rows 402 comprises a plurality of straight angled sections 406a, 406b arranged end-to-end in a zig-zag or herringbone pattern extending from the lower (upstream edge) to the upper (downstream edge) of the sealing member 400. In alternative embodiments, the rows 402 can be sinusoidal-shaped rows having curved longitudinal edges.

Figure 42:
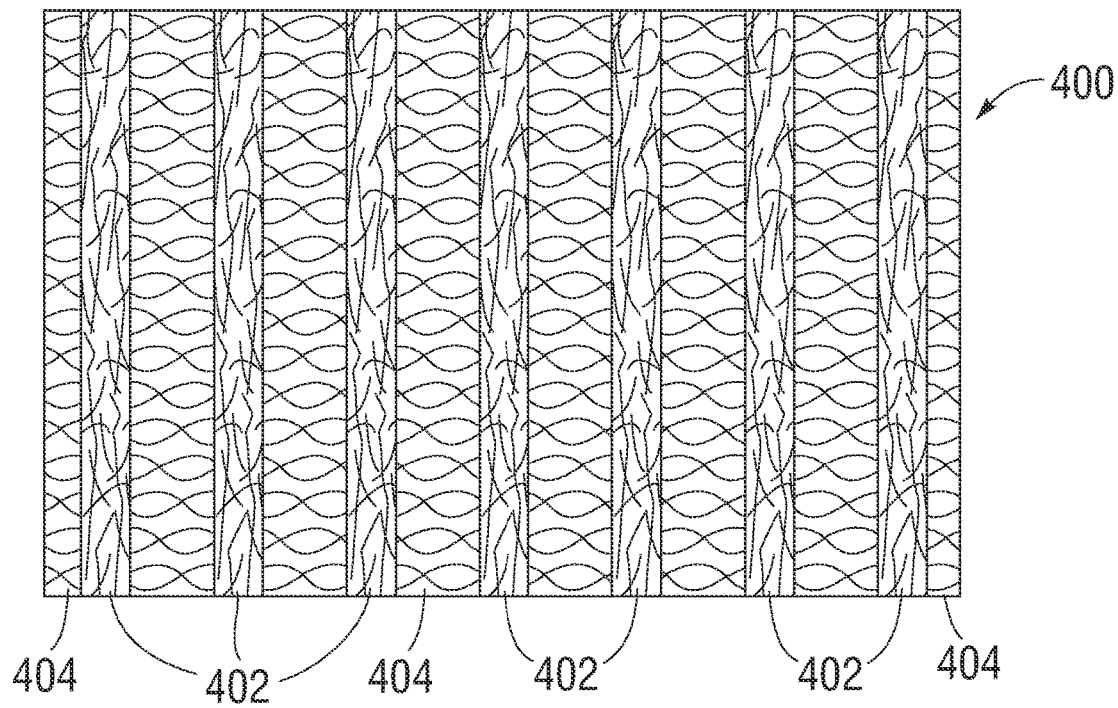
FIG. 42 is a flattened view of the outer sealing member of FIG. 41 shown in an axially elongated, tensioned state when the prosthetic heart valve is in a radially compressed state for delivery.

When the prosthetic valve is crimped to its radially compressed state, the frame 12 elongates, causing the sealing member to stretch in the axial direction, as depicted in FIG. 42, to its second configuration. The lower-density rows 404 facilitate elongation of the sealing member and permit straightening of the higher-density rows 402. FIG. 42 depicts the higher-density rows 402 as straight sections extending from the inflow edge to the outflow edge of the sealing member. However, it should be understood that the higher-density rows 402 need not form perfectly straight rows when the prosthetic valve is in the radially compressed state. Instead, "straightening" of the higher-density rows 402 occurs when the angle 408 between adjacent angled segments 406a, 406b of each row increases upon axial elongation of the sealing member.

The varying stitch density of the sealing member 400 reduces overall bulkiness of the sealing member to minimize the crimp profile of the prosthetic valve. The zig-zag or undulating pattern of the higher-density rows 402 in the radially expanded state of the prosthetic valve facilitates stretching of the sealing member in the axial direction upon radial compression of the prosthetic valve and allows the sealing member to return to its pre-stretched state in which the sealing member fits snugly around the frame upon radial expansion of the prosthetic valve. Additionally, the zig-zag or undulating pattern of the higher-density rows 402 in the radially expanded state of the prosthetic valve eliminates any straight flow paths for blood between adjacent rows 402 extending along the outer surface of the sealing member from its outflow edge to its inflow edge to facilitate sealing and tissue ingrowth with surrounding tissue.

In alternative embodiments, a sealing member 400 can have a plurality of circumferentially extending higher-density rows (like rows 402 but extending in the circumferential direction) interspersed with a plurality of circumferentially extending lower-density rows (like rows 404 but extending in the circumferential direction). In some embodiments, a sealing member 400 can have axially-extending and circumferential-extending higher-density rows interspersed with axially-extending and circumferential-extending lower-density rows.

FIGS. 43A, 43B, 44A, and 44B illustrate an outer sealing member 500 for a prosthetic heart valve (e.g., a prosthetic heart valve 10), according to another embodiment. The sealing member 500 can have a plush exterior surface 504. The sealing member 500 can be secured to a frame 12 of the prosthetic valve using, for example, sutures, ultrasonic welding, or any other suitable attachment method as previously described herein. For purposes of illustration, enlarged or magnified portions of the sealing member 500 are shown in the figures. It should be understood that the overall size and shape of the sealing member 500 can be modified as needed to cover the entire outer surface of the frame 12 or portion of the outer surface of the frame, as previously described herein.

The sealing member 500 can comprise a woven or knitted fabric. The fabric can be resiliently stretchable between a first, natural, or relaxed configuration (FIG. 43A), and a second, axially elongated, or tensioned configuration (FIG. 43B). When disposed on the frame 12, the relaxed configuration can correspond to the radially expanded, functional configuration of the prosthetic valve, and the elongated configuration can correspond to the radially collapsed delivery configuration of the prosthetic valve. Thus, with reference to FIG. 43A, the sealing member 500 can have a first length $L_1$ in the axial direction when the prosthetic valve is in the radially expanded configuration, and a second length $L_2$ (FIG. 43B) in the axial direction that is longer than $L_1$ when the valve is crimped to the delivery configuration, as described in greater detail below.

The fabric can comprise a plurality of circumferentially extending warp yarns 512 and a plurality of axially extending weft yarns 514. In some embodiments, the warp yarns 512 can have a denier of from about 1 D to about 300 D, about 10 D to about 200 D, or about 10 D to about 100 D. In some embodiments, the warp yarns 512 can have a thickness $t_1$ (FIG. 44A) of from about 0.01 mm to about 0.5 mm, about 0.02 mm to about 0.3 mm, or about 0.03 mm to about 0.1 mm. In some embodiments, the warp yarns 512 can have a thickness $t_1$ of about 0.03 mm, about 0.04 mm, about 0.05 mm, about 0.06 mm, about 0.07 mm, about 0.08 mm, about 0.09 mm, or about 0.1 mm. In a representative embodiment, the warp yarns 512 can have a thickness of about 0.06 mm.

The weft yarns 514 can be texturized yarns comprising a plurality of texturized filaments 516. For example, the filaments 516 of the weft yarns 514 can be bulked, wherein, for example, the filaments 516 are twisted, heat set, and untwisted such that the filaments retain their deformed, twisted shape in the relaxed, non-stretched configuration. The filaments 516 can also be texturized by crimping, coiling, etc. When the weft yarns 514 are in a relaxed, non-tensioned state, the filaments 516 can be loosely packed and can provide compressible volume or bulk to the fabric, as well as a plush surface. In some embodiments, the weft yarns 514 can have a denier of from about 1 D to about 500 D, about 10 D to about 400 D, about 20 D to about 350 D, about 20 D to about 300 D, or about 40 D to about 200 D. In certain embodiments, the weft yarns 514 can have a denier of about 150 D. In some embodiments, a filament count of the weft yarns 514 can be from 2 filaments per yarn to 200 filaments per yarn, 10 filaments per yarn to 100 filaments per yarn, 20 filaments per yarn to 80 filaments per yarn, or about 30 filaments per yarn to 60 filaments per yarn. Additionally, although the axially-extending textured yarns 514 are referred to as weft yarns in the illustrated configuration, the fabric may also be manufactured such that the axially-extending textured yarns are warp yarns and the circumferentially-extending yarns are weft yarns.

Figure 44A:
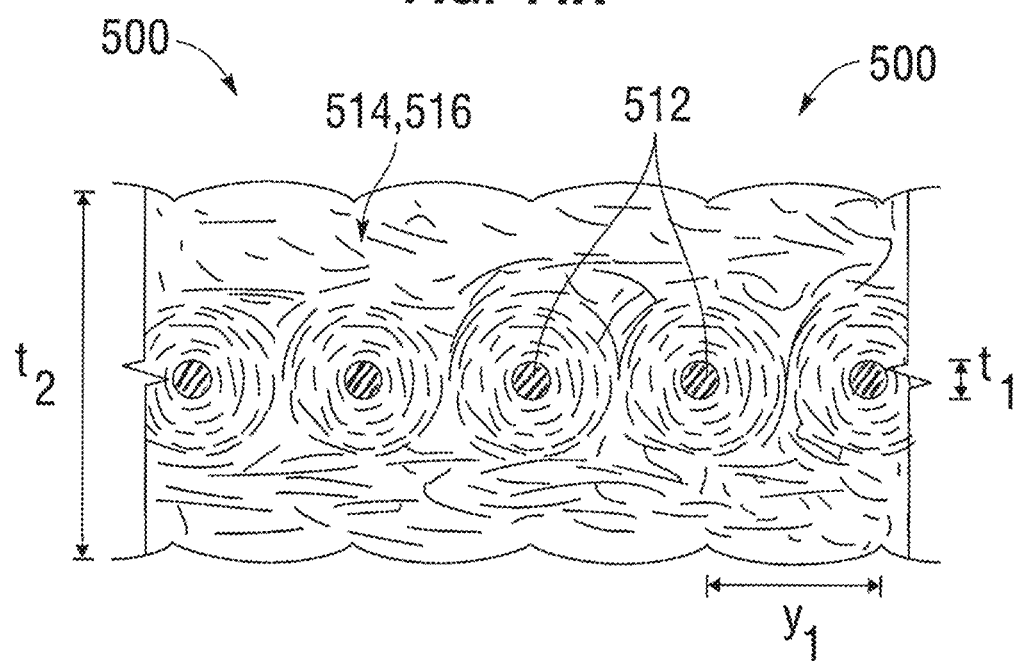
FIG. 44A is a cross-sectional view of the fabric of the sealing member of FIG. 43A in a relaxed state.
Figure 44B:
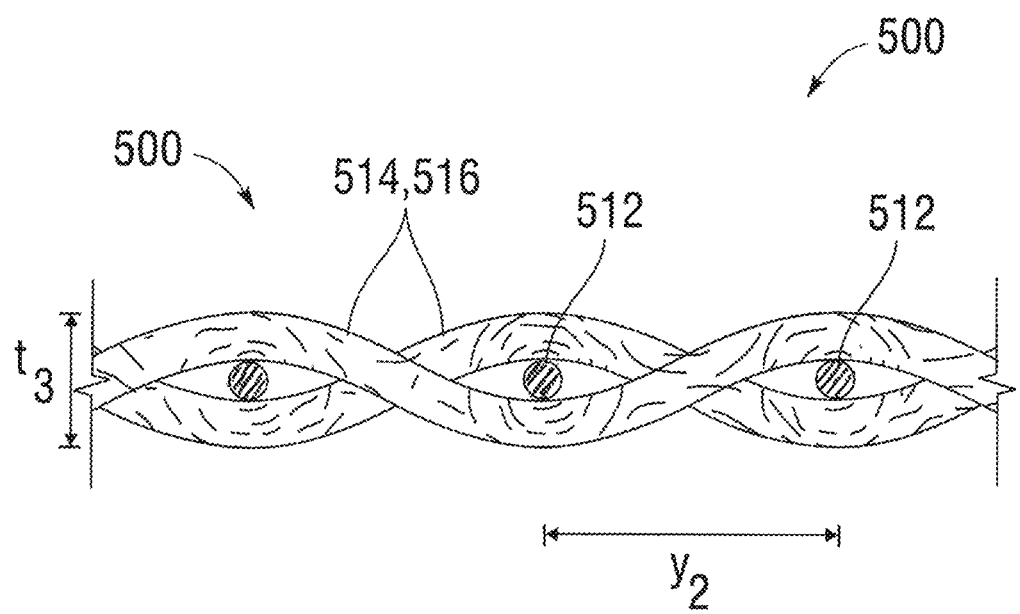
FIG. 44B is a cross-sectional view of the fabric of the sealing member of FIG. 43B in a tensioned state.

FIGS. 44A and 44B illustrate a cross-sectional view of the sealing member in which the weft yarns 512 extend into the plane of the page. With reference to FIG. 44A, the fabric of the sealing member 500 can have a thickness $t_2$ of from about 0.1 mm to about 10 mm, about 1 mm to about 8 mm, about 1 mm to about 5 mm, about 1 mm to about 3 mm, about 0.5 mm, about 1 mm, about 1.5 mm, about 2 mm, about 2.5 mm, or about 3 mm when in a relaxed state and secured to a frame. In some embodiments, the sealing member 500 can have a thickness of about 0.1 mm, about 0.2 mm, about 0.3 mm, about 0.4 mm, or about 0.5 mm as measured in a relaxed state with a weighted drop gauge having a presser foot. In a representative example, the sealing member can have a thickness of about 1.5 mm when secured to a prosthetic valve frame in the relaxed state. The texturized, loosely packed filaments 516 of the weft yarns 514 in the relaxed state can also promote tissue growth into the sealing member 500.

Figure 43A:
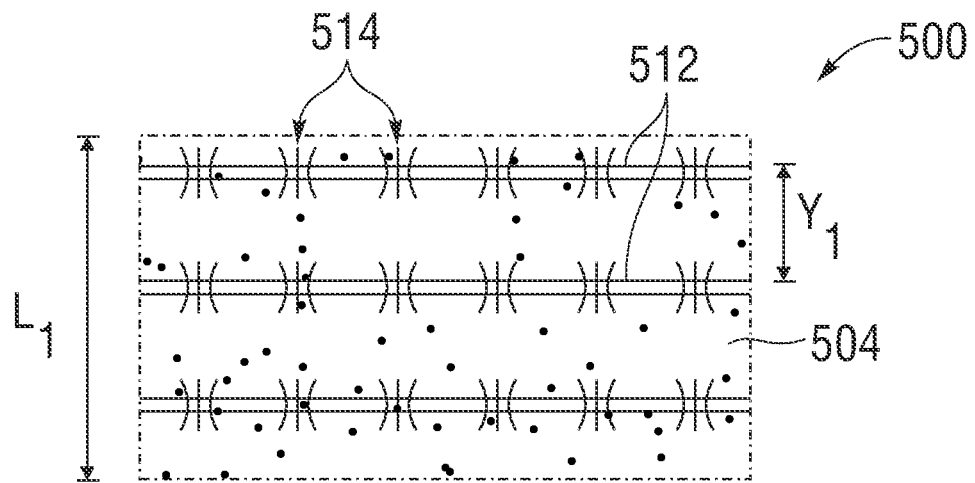
FIG. 43A is a magnified view of a portion of another embodiment of an outer sealing member for a prosthetic heart valve, wherein the sealing member is shown in a relaxed state when the prosthetic heart valve is radially expanded to its functional size.
Figure 43B:
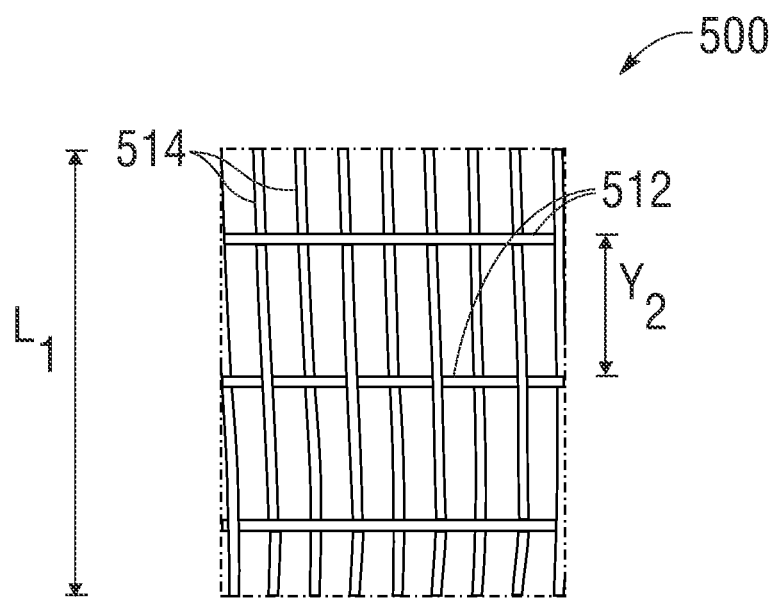
FIG. 43B is a magnified view of the sealing member of FIG. 43A shown in an axially elongated, tensioned state when the prosthetic heart valve is in a radially compressed state for delivery.

When the fabric is in the relaxed state, the textured filaments 516 of the weft yarns 514 can be widely dispersed such that individual weft yarns are not readily discerned, as depicted in FIG. 43A. When tensioned in the axial direction, the filaments 516 of the weft yarns 514 can be drawn together as the weft yarns elongate and the kinks, twists, etc., of the filaments are pulled straight such that the fabric is stretched and the thickness decreases. In certain embodiments, when sufficient tension is applied to the fabric in the axial direction (the weft direction in the illustrated embodiment), such as when the prosthetic valve is crimped onto a shaft of a delivery apparatus, the textured fibers 516 can be pulled together such that individual weft yarns 514 become discernable, as best shown in FIG. 43B.

Thus, for example, when fully stretched, the sealing member can have a second thickness $t_3$, as shown in FIG. 44B that is less than the thickness $t_2$. In certain embodiments, the thickness of the tensioned weft yarns 514 may be the same or nearly the same as the thickness $t_1$ of the warp yarns 512. Thus, in certain examples, when stretched the fabric can have a thickness $t_3$ that is the same or nearly the same as three times the thickness $t_1$ of the warp yarns 512 depending upon, for example, the amount of flattening of the weft yarns 514. Accordingly, in the example above in which the warp yarns 512 have a thickness of about 0.06 mm, the thickness of the sealing member can vary between about 0.2 mm and about 1.5 mm as the fabric stretches and relaxes. Stated differently, the thickness of the fabric can vary by 750% or more as the fabric stretches and relaxes.

Additionally, as shown in FIG. 44A, the warp yarns 512 can be spaced apart from each other in the fabric by a distance $y_1$ when the outer covering is in a relaxed state. As shown in FIGS. 43B and 44B, when tension is applied to the fabric in the direction perpendicular to the warp yarns 512 and parallel to the weft yarns 514, the distance between the warp yarns 512 can increase as the weft yarns 514 lengthen. In the example illustrated in FIG. 44B, in which the fabric has been stretched such that the weft yarns 514 have lengthened and narrowed to approximately the diameter of the warp yarns 512, the distance between the warp yarns 512 can increase to a new distance $y_2$ that is greater than the distance $y_1$.

In certain embodiments, the distance $y_1$ can be, for example, about 1 mm to about 10 mm, about 2 mm to about 8 mm, or about 3 mm to about 5 mm. In a representative example, the distance $y_1$ can be about 3 mm. In some embodiments, when the fabric is stretched as in FIGS. 43B and 44B, the distance $y_2$ can be about 6 mm to about 10 mm Thus, in certain embodiments, the length of the sealing member 500 in the axial direction can vary by 100% or more between the relaxed length $L_1$ and the fully stretched length (e.g., $L_2$). The fabric's ability to lengthen in this manner facilitates crimping of the prosthetic valve. Thus, the sealing member 500 can be soft and voluminous when the prosthetic valve is expanded to its functional size, and relatively thin when the prosthetic valve is crimped to minimize the overall crimp profile of the prosthetic valve.

GENERAL CONSIDERATIONS

It should be understood that the disclosed embodiments can be adapted to deliver and implant prosthetic devices in any of the native annuluses of the heart (e.g., the pulmonary, mitral, and tricuspid annuluses), and can be used with any of various approaches (e.g., retrograde, antegrade, transseptal, transventricular, transatrial, etc.). The disclosed embodiments can also be used to implant prostheses in other lumens of the body. Further, in addition to prosthetic valves, the delivery assembly embodiments described herein can be adapted to deliver and implant various other prosthetic devices such as stents and/or other prosthetic repair devices.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

As used herein, operations that occur "simultaneously" or "concurrently" occur generally at the same time as one another, although delays in the occurrence of one operation relative to the other due to, for example, spacing, play or backlash between components in a mechanical linkage such as threads, gears, etc., are expressly within the scope of the above terms, absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A prosthetic heart valve comprising:
    an annular frame that is radially collapsible to a collapsed configuration and radially expandable to an expanded configuration, the frame having a plurality of circumferentially extending rows of angled struts, including a first row of angled struts defining an inflow end of the frame, a second row of angled struts downstream of the first row, a third row of angled struts downstream of the second row, a fourth row of angled struts downstream of the third row, and a fifth row of angled struts downstream of the fourth row, each row of angled struts comprising angled struts arranged in a zig-zag pattern;
    a leaflet structure comprising three leaflets forming three commissures of the leaflet structure, wherein the commissures are connected to the frame; and
    an annular outer sealing member extending around an outer surface of the frame, the sealing member having an inflow edge portion secured to the struts of the first row with sutures and an outflow edge portion having a plurality of tapered projections secured with sutures to the struts of a selected one of the second, third, or fourth row of angled struts, wherein the projections are shaped to correspond to the zig-zag pattern of the selected row of struts;

wherein the outer sealing member is configured to stretch axially when the frame is radially compressed to the collapsed configuration;

wherein the outer sealing member comprises a fabric comprising an inner mesh layer and an outer pile layer, wherein the mesh layer comprises a plurality of circumferentially extending first rows of interlaced yarns alternating with a plurality of circumferentially extending second rows of interlaced yarns, wherein the first rows have a density greater than the second rows, and wherein the pile layer is formed from yarns extending from and interlaced with the mesh layer.

2. The prosthetic heart valve of claim 1, wherein the frame is made of a plastically-expandable material.

3. The prosthetic heart valve of claim 2, wherein the plastically-expandable material comprises a nickel cobalt chromium alloy.

4. The prosthetic heart valve of claim 1, wherein the frame is made of nitinol.

5. The prosthetic heart valve of claim 1, further comprising an annular inner skirt extending along an inner surface of the frame, wherein the inner skirt comprises an inflow edge portion and an outflow edge portion, wherein the inflow edge portion of the inner skirt is secured to the struts of the first row of angled struts with sutures.

6. The prosthetic heart valve of claim 5, wherein the outflow edge portion of the inner skirt is secured with sutures to selected struts of the frame downstream of the outflow edge portion of the outer sealing member.

7. The prosthetic heart valve of claim 5, wherein the outer sealing member has an outer surface and the inner skirt has an outer surface, wherein the outer surface of the outer sealing member has a different surface texture than the outer surface of the inner skirt.

8. A prosthetic heart valve comprising:
an annular frame that is radially collapsible to a collapsed configuration and radially expandable to an expanded configuration, the frame having a plurality of circumferentially extending rows of angled struts, each row of angled struts comprising angled struts arranged in a zig-zag pattern;
a leaflet structure comprising three leaflets forming three commissures of the leaflet structure, wherein the commissures are connected to the frame; and
an annular outer sealing member extending around an outer surface of the frame, the sealing member having an inflow edge portion and an undulating outflow edge portion that is connected to and shaped to correspond to the zig-zag pattern of one of the rows of angled struts, wherein the outflow edge portion defines a plurality of tapered projections;
wherein the outer sealing member comprises a mesh layer and a pile layer comprising a plurality of pile yarns extending outwardly from the mesh layer;
an annular inner skirt extending along an inner surface of the frame, wherein the inner skirt comprises an inflow edge portion and an outflow edge portion;
wherein the inflow edge portion of the inner skirt is wrapped around an inflow end of the frame and extends partially over an outer surface of the pile layer along the inflow edge portion of the outer sealing member, and wherein the inflow edge portion of the outer sealing member is stitched to the inflow end portion of the inner skirt at an inflow end of the frame such that the pile layer is compressed by the inflow edge portion of the inner skirt where it extends over the pile layer;
wherein the inner skirt extends axially further toward an outflow end of the frame than the outer sealing member, wherein the outflow end portion of the inner skirt is connected to and shaped to correspond to the zig-zag pattern of another one of the rows of angled struts downstream of the outflow end portion of the outer sealing member.

9. The prosthetic heart valve of claim 8, wherein the sealing member is configured to stretch axially when the frame is radially compressed to the collapsed configuration.

10. The prosthetic heart valve of claim 8, wherein the sealing member comprises a fabric.

11. The prosthetic heart valve of claim 8, wherein the frame is made of nitinol and is self-expandable from the collapsed configuration to the expanded configuration.

12. The prosthetic heart valve of claim 8, wherein the rows of angled struts include a first row of angled struts defining an inflow end of the frame, a second row of angled struts downstream of the first row, a third row of angled struts downstream of the second row, a fourth row of angled struts downstream of the third row, and a fifth row of angled struts downstream of the fourth row.

13. The prosthetic heart valve of claim 12, wherein the outflow edge portion of the outer sealing member is attached to the struts of the third row with sutures.

14. The prosthetic heart valve of claim 13, wherein the outflow edge portion of the inner skirt is secured to struts of the fifth row of angled struts with sutures.

15. A prosthetic heart valve comprising:
an annular frame that is radially collapsible to a collapsed configuration and radially expandable to an expanded configuration, the frame having a plurality of circumferentially extending rows of angled struts, including a first row of angled struts defining an inflow end of the frame, a second row of angled struts downstream of the first row, a third row of angled struts downstream of the second row, a fourth row of angled struts downstream of the third row, and a fifth row of angled struts downstream of the fourth row, each row of angled struts comprising angled struts arranged in a zig-zag pattern;
a leaflet structure comprising three leaflets forming three commissures of the leaflet structure, wherein the commissures are connected to the frame; and
an annular outer sealing member extending around an outer surface of the frame, the sealing member having an inflow edge portion and an outflow edge portion having a plurality of tapered projections secured with sutures to the struts of the third row of angled struts, wherein the projections are shaped to correspond to the zig-zag pattern of the third row of struts, wherein each strut of the third row has an upper end connected to an upper end of an adjacent strut at a first junction and a lower end connected to a lower end of an adjacent strut at a second junction;
wherein each projection comprises two angled side edges that converge at a peak of the projection and each side edge converges with an adjacent side edge of an adjacent projection at a valley between adjacent projections, wherein each peak is positioned at a first junction and each valley is positioned at a second junction;
wherein each side edge of a projection is secured to an adjacent strut of the third row of angled struts with multiple stitches that extend around the adjacent strut at locations along a length of the strut between each first junction and an adjacent second junction such that each side edge is secured to an adjacent strut along an entire length of the side edge; and an annular inner skirt extending along an inner surface of the frame, wherein the inner skirt comprises an inflow edge portion and an outflow edge portion, wherein the inflow edge portion of the inner skirt is secured to the struts of the first row of angled struts with sutures, wherein the inner skirt extends axially further toward an outflow end of the frame than the outer sealing member;

wherein the outer sealing member is configured to stretch axially when the frame is radially compressed to the collapsed configuration;

wherein the inflow edge portion of the outer sealing member is stitched to the inflow edge portion of the inner skirt at the inflow end of the frame;

wherein the outer sealing member comprises a knitted fabric comprising a plurality of circumferentially extending first rows of relatively higher-density stitching spaced apart by a plurality of circumferentially extending second rows of relatively lower-density stitching.

16. The prosthetic heart valve of claim 15, wherein the outflow edge portion of the inner skirt is secured to struts of the fifth row of angled struts with sutures.

\* \* \* \* \*